US010456026B2

(12) United States Patent
Neal et al.

(10) Patent No.: US 10,456,026 B2
(45) Date of Patent: *Oct. 29, 2019

(54) APPARATUS, SYSTEM, AND METHOD FOR INTRAOCULAR LENS POWER CALCULATION USING A REGRESSION FORMULA INCORPORATING CORNEAL SPHERICAL ABERRATION

(71) Applicant: AMO WaveFront Sciences, LLC, Albuquerque, NM (US)

(72) Inventors: Daniel R. Neal, Tijeras, NM (US); Thomas D. Raymond, Edgewood, NM (US); Richard J. Copland, Albuquerque, NM (US); Wei Xiong, Albuquerque, NM (US); Stephen W. Farrer, Albuquerque, NM (US); Paul D. Pulaski, Albuquerque, NM (US); Daniel R. Hamrick, Cedar Crest, NM (US); Carmen Canovas Vidal, Groningen (NL); Pablo Artal, Murcia (ES)

(73) Assignee: AMO WaveFront Sciences, LLC, Albuquerque, NM (US)

( * ) Notice: Subject to any disclaimer, the term of this patent is extended or adjusted under 35 U.S.C. 154(b) by 409 days.

This patent is subject to a terminal disclaimer.

(21) Appl. No.: 15/098,125

(22) Filed: Apr. 13, 2016

(65) Prior Publication Data
US 2016/0227996 A1 Aug. 11, 2016

Related U.S. Application Data

(60) Continuation-in-part of application No. 14/148,420, filed on Jan. 6, 2014, now Pat. No. 9,393,108, which
(Continued)

(51) Int. Cl.
A61B 3/00 (2006.01)
A61B 3/107 (2006.01)
(Continued)

(52) U.S. Cl.
CPC .............. *A61B 3/0025* (2013.01); *A61B 3/10* (2013.01); *A61B 3/1005* (2013.01); *A61B 3/107* (2013.01);
(Continued)

(58) Field of Classification Search
CPC ........... A61B 3/10; A61B 3/103; A61B 3/107; A61B 3/117; A61B 3/1005; A61B 3/0025;
(Continued)

(56) References Cited

U.S. PATENT DOCUMENTS 5,777,718 A 7/1998 Kohayakawa
6,052,180 A 4/2000 Neal et al.
(Continued)

FOREIGN PATENT DOCUMENTS

CN 1951340 A 4/2007
WO 2006053216 A2 5/2006
(Continued)

OTHER PUBLICATIONS

International Search Report and Written Opinion for Application No. PCT/US2017/027489, dated Oct. 4, 2017, 12 pages.
(Continued)

Primary Examiner — William H Matthews
(74) Attorney, Agent, or Firm — Johnson & Johnson Surgical Vision, Inc.

(57) ABSTRACT

A system for predicting optical power for an intraocular lens based upon measured biometric parameters in a patient's eye includes: a biometric reader capable of measuring one or more biometric parameters of the patient's eye and obtaining
(Continued)

at least one value for at least one of the one or more biometric parameters, and further measuring a representation of a corneal topography of the patient's eye; a processor; and a computer readable medium coupled to the processor and having stored thereon a program that upon execution causes the processor to: receive the at least one value; obtain a corneal spherical aberration (SA) based upon the representation of the corneal topography; and calculate an optimized optical power to obtain a desired postoperative condition by applying the received at least one value and the obtained corneal spherical aberration to a modified regression.

28 Claims, 32 Drawing Sheets

Related U.S. Application Data is a division of application No. 12/969,060, filed on Dec. 15, 2010, now Pat. No. 8,623,081.

(51) Int. Cl.
*A61B 3/10* (2006.01)
*A61F 2/16* (2006.01)

(52) U.S. Cl.
CPC .............. *A61F 2/16* (2013.01); *A61F 2/1637* (2013.01); *A61F 2240/002* (2013.01)

(58) Field of Classification Search
CPC .... A61F 2009/00878; A61F 2009/0088; A61F 2009/00882; A61F 2009/00897; A61F 9/007; A61F 2/1637
See application file for complete search history.

(56) References Cited

U.S. PATENT DOCUMENTS

| | | |
|---|---|---|
| 6,130,419 A | 10/2000 | Neal |
| 6,609,793 B2 | 8/2003 | Norrby et al. |
| 6,634,750 B2 | 10/2003 | Neal et al. |
| 6,908,196 B2 | 6/2005 | Herekar et al. |
| 7,044,604 B1 | 5/2006 | Arrowsmith |
| 7,455,407 B2 | 11/2008 | Neal et al. |
| 7,553,022 B2 | 6/2009 | Neal et al. |
| 7,980,699 B2 | 7/2011 | Neal et al. |
| 7,988,290 B2 | 8/2011 | Campbell et al. |
| 7,988,292 B2 | 8/2011 | Neal et al. |
| 8,126,246 B2 | 2/2012 | Farrer et al. |
| 8,260,024 B2 | 9/2012 | Farrer et al. |
| 2006/0030938 A1 | 2/2006 | Altmann |
| 2007/0260157 A1 | 11/2007 | Norrby |
| 2012/0158132 A1 | 6/2012 | Canovas et al. |

FOREIGN PATENT DOCUMENTS

| | | |
|---|---|---|
| WO | 2010028654 A1 | 3/2010 |
| WO | 2012024152 A1 | 2/2012 |

OTHER PUBLICATIONS

Applegate R.A., et al., "Interaction Between Aberrations to Improve or Reduce Visual Performance," Journal of Cataract and Refractive Surgery, 2003, vol. 29 (8), pp. 1487-1495.

Beiko G.H., et al., "Distribution of Corneal Spherical Aberration in a Comprehensive Ophthalmology Practice and Whether Keratometry can Predict Aberration Values," Journal of Cataract and Refractive Surgery, 2007, vol. 33 (5), pp. 848-858.

International Search Report and Written Opinion for Application No. PCT/US2011/064914, dated Mar. 19, 2012, 13 pages.

Wang L., et al., "Evaluation of Intraocular Lens Power Prediction Methods Using the American Society of Cataract and Refractive Surgeons Post-Keratorefractive Intraocular Lens Power Calculator," Journal of Cataract and Refractive Surgery, 2010, vol. 36 (9), pp. 1466-1473.

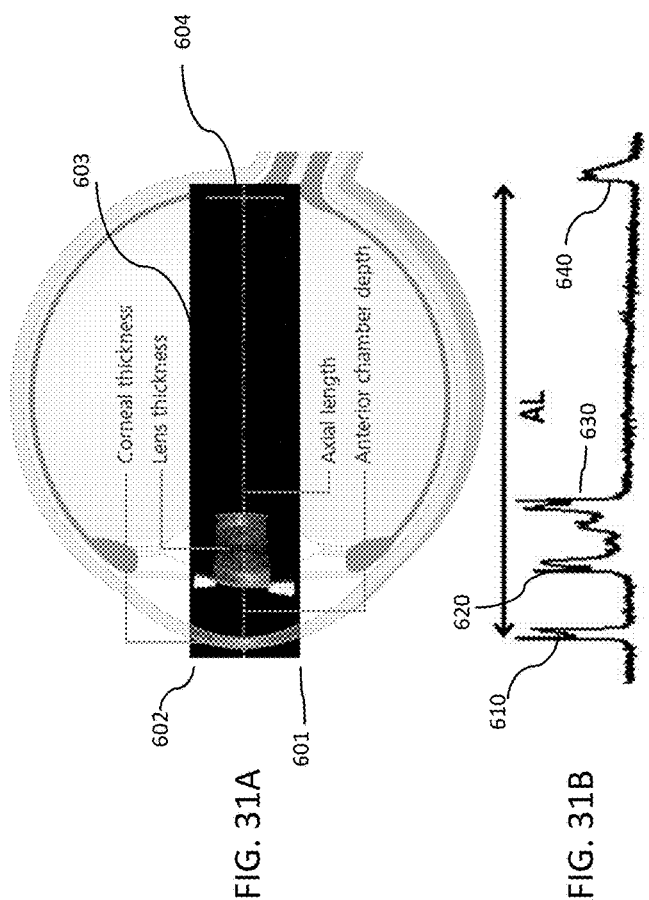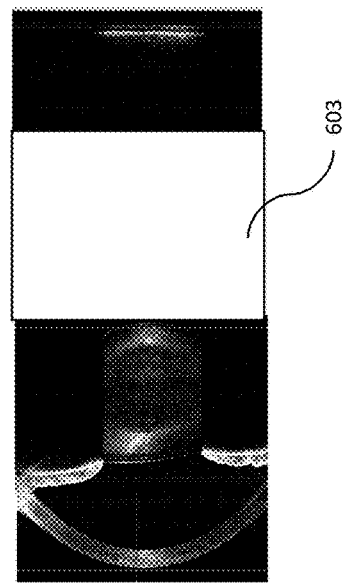
FIG. 31A  FIG. 31B  FIG. 31C

APPARATUS, SYSTEM, AND METHOD FOR INTRAOCULAR LENS POWER CALCULATION USING A REGRESSION FORMULA INCORPORATING CORNEAL SPHERICAL ABERRATION

CROSS-REFERENCE TO RELATED APPLICATIONS

This application is a continuation-in-part of U.S. patent application Ser. No. 14/148,420, filed Jan. 6, 2014, now U.S. Pat. No. 9,393,108, which is a divisional application of U.S. application Ser. No. 12/969,060, filed on Dec. 15, 2010, now U.S. Pat. No. 8,623,081, all of which applications are hereby incorporated by reference in their entirety.

FIELD OF THE INVENTION

The present invention relates generally to power calculations for intraocular lenses (IOLs) and, more particularly, is directed to an apparatus, system and method to develop and use a regression formula incorporating corneal spherical aberrations in order to select a suitable power for an IOL to be implanted into an eye in order to obtain a predetermined refractive outcome.

BACKGROUND OF THE INVENTION

Intraocular Lenses (IOLs) are frequently used for restoring or improving visual performance, such as after cataract surgery. Because an IOL may be selected from various providers and in differing IOL powers, reliable systems and methods to select IOL powers to achieve the desired refractive outcome for a patient are needed. More particularly, it is most desirable to select an IOL power that will achieve emmetropia after surgery, independent of the refractive state or clinical history of the patient prior to implantation. The term emmetropia, and variations thereof, is used herein to indicate a state of vision in which an object at infinite distance from the subject eye is in sharp focus on the patient's retina.

The IOL power necessary to achieve emmetropia is often calculated using regression theory. One of the first calculations using this approach was the Saunders, Retzlaff, and Kraff formula (SRK). It is a regression formula empirically derived from clinical data to indicate the optimal power for an IOL. The SRK regression formula is:

$$P = A - 2.5 * AXL - 0.9 * K$$

where P is the IOL power, A is the lens constant, AXL is the axial length in millimeters, and K is the average corneal power in diopters. Unfortunately, the SRK regression formula may lead to the indication of a stronger IOL power for long eyes, and a weaker IOL power for short eyes. That is, the SRK typically underestimates the necessary IOL power to obtain emmetropia for short eyes, and overestimates the IOL power necessary for long eyes.

In order to remedy these shortcomings of SRK, the SRKII regression formula was developed, incorporating further empirical analysis of clinical data. In the SRKII regression, an additional constant is provided to modify the lens constant A from the SRK formula. The modification to A is based on whether the eye is long or short. More particularly, the SRKII formula is:

$$P = A - 2.5 * AXL - 0.9 * K + F$$

where F is a known constant that is equal to +3 D at less than 20 millimeters of axial length (AXL), +2 D at 20 to 20.9 millimeters, +1 D at 21 to 21.9 millimeters, 0 D at 22 to 22.5 millimeters, and −0.5 D at greater than 24.5 millimeters. By way of example, if SRK yields an IOL power of +32 D, SRKII may yield an IOL power of +35 D (+32 D+3 D=+35 D), if the patient's axial length is less than 20 mm.

An additional regression method, developed in an effort to address the shortcomings of SRK and SRKII, is the SRK/T formula. In the SRK/T method, the empirical calculation based on regressions is used to predict the position of the IOL in the eye after surgery. Once the position is known, the IOL power to implant is calculated by simple paraxial optics, taking into account that the eye can be modeled under this approximation as a two lens system (wherein the two lenses are the cornea and the IOL), focusing on the retina. This approach is based on Fyodorov's theoretical formula.

There are numerous formulas for calculating IOL power, such as the aforementioned, and additionally the Haigis, Olsen, and Holladay 1 and 2 models, for example. An in-depth analysis of IOL power calculation methods is provided in Shammas H J (ed.), *Intraocular Lens Power Calculations*, Thorofare, N.J.; Slack (2004), which is incorporated herein by reference as if set forth in its entirety.

However, it is well known that these formulas do not provide accurate predictions to achieve emmetropia for all preoperative refractive states. While a good prediction may be obtained using some of the aforementioned formulas to achieve emmetropia after surgery for emmetropic or close to emmetropic patients prior to surgery, errors arise for those with extreme myopia or hyperopia. These deviations for extreme eyes are not unexpected, because empirical regressions have been back calculated from "average," that is, emmetropic or near-emmetropic, eyes. Due to the regression nature of these formulas, even emmetropic eyes with a non common or odd configuration may not be well predicted, since they are not inside of the regression. Thus, it is also possible to have errors in emmetropic eyes.

For example, FIG. 1 illustrates the variations from the predicted outcome, for the same patient (labeled by patient number), provided by different regression calculation methods. As illustrated, the differences from the predicted outcome for a particular patient using the IOL power recommended by the current regression calculations become more extreme for progressively more myopic eyes (i.e., eyes having an average IOL power predicted of less than 15 D) or hyperopic eyes (i.e., eyes having an average IOL power predicted of greater than 25 D).

The way in which these deviations from the piano refraction are typically approached is by the optimization of the A constant. Thus, possible bias, as well as, surgical technique can be considered by personalizing this constant. This approach can remove small biases, so that the average population can have zero refraction after surgery. However, the standard deviation is not lowered, meaning that IOL power for those non average eyes is still not correctly predicted.

Postlasik eyes are a particular example of eyes that are not "average," in part because the corneal power of the postlasik eye has been modified by lasik surgery. A factor that causes difficulty in obtaining an optimal IOL power outcome for the post-lasik eye is the corneal power (K) in the regression formulas above, which is often incorrectly measured by topographers or keratometers after a lasik procedure. Additionally, the decoupling that occurs between the anterior and posterior corneal radius after lasik makes the effective index calculated for "average" patients inaccurate for postlasik eyes. Thus, it is well known that regression formulas do not typically provide a recommended IOL power that will produce the desired refractive outcome for post-lasik patients and thus regular regression formulas cannot be directly applied to this population without modification.

Moreover, it has been widely reported that the lasik procedure may typically generate large amounts of corneal aberrations. This may be inferred because post-lasik patients typically present higher amounts of corneal aberrations, likely due to the lasik surgery, than would an "average" patient. Such aberrations should not be excluded in IOL power predictions if the desired refractive outcome is to be obtained. Currently, aberrations are not incorporated in regression formulas, which are instead based on paraxial optics as discussed above.

The importance of corneal aberrations in IOL power calculations has been demonstrated in, for example, Application 61/375,657 filed on Aug. 20, 2010 entitled "Apparatus, System and Method for an Empirically-Based, Customized Intraocular Lens Power Calculation". The ray tracing approach is based on the exact solution of Snell's law for all of the rays passing through the ocular surfaces placed in positions defined by biometric measurements. This is a personalized model, where all the patient's biometric measurements are considered, in contrast with regression formulas, which are based on averages. In this customized model, all corneal aberrations can also be introduced, thus making it applicable for both normal and postlasik patients, for example.

FIG. 2 shows the residual refraction (SE meaning spherical equivalent) achieved by different approaches including the SRK/T as well as the ray tracing approach with and without corneal aberrations for 17 normal patients. Because of the small amount of aberrations, the impact on IOL power calculation is limited.

FIG. 3 shows the improvement in IOL power prediction considering corneal aberration (custom+ab) in the ray tracing approach with respect to the current state of the art in IOL power calculation for postlasik eyes (double K) and also with the same ray tracing procedure without considering corneal wavefront aberrations for 12 patients. FIG. 4 reveals that this improvement is related to the lower standard deviation, so IOL power calculations can be more predictable and accurate when corneal aberrations are considered. FIG. 5 discloses that the improvement in the accuracy of IOL power calculations considering corneal aberrations is mainly due to spherical aberration (z12), since this parameter is highly correlated with the difference in IOL power prediction with and without considering corneal aberrations (CWA_influence).

Although ray tracing may be the most theoretically accurate way to calculate IOL power, all inputs must be very accurate, since there is not an A constant to optimize in case of errors or bias. Another disadvantage of this procedure is that is relatively slow, since the area under the radial MTF is used as an optimized parameter and the computation for this parameter takes time.

Thus, the need exists for an apparatus, system and method that provide greater accuracy in predicting optimal IOL power for particular patients using regression theory, for eyes inside and outside the "average" range.

BRIEF DESCRIPTION OF THE FIGURES

Embodiments of the present invention will be understood with reference to the detailed description in conjunction with the accompanying figures, in which like numerals indicate like aspects, and wherein:

FIG. 31A illustrates a preferred scanning region for the OCT subsystem according to many embodiments of the present invention.

FIG. 31B shows a representative graph of an intensity of an OCT signal of an OCT subsystem 190 according to many embodiments as a function of depth along the axis defining the axial length of the eye.

FIG. 31C shows a cross-section of an eye obtained by an optical measurement system of the present invention using an OCT subsystem according to the present invention.

SUMMARY OF THE INVENTION

Figure 1:
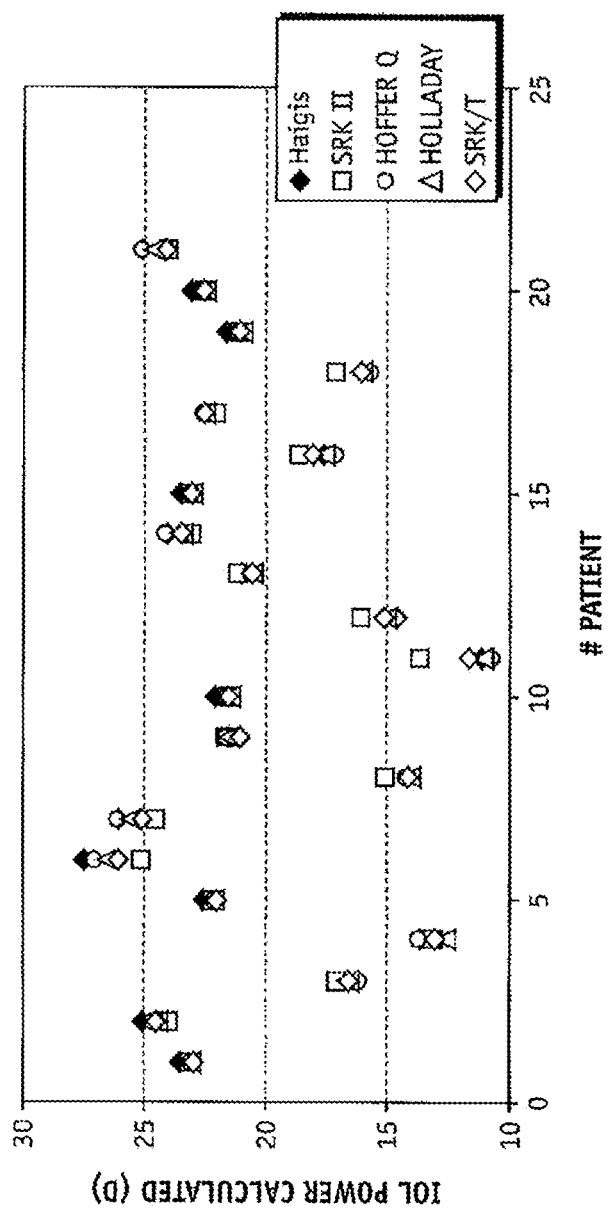
FIG. 1 is a histogram illustrating required IOL power predicted by prior art regression models for normal patient that have not undergone cataract surgery.
Figure 2:
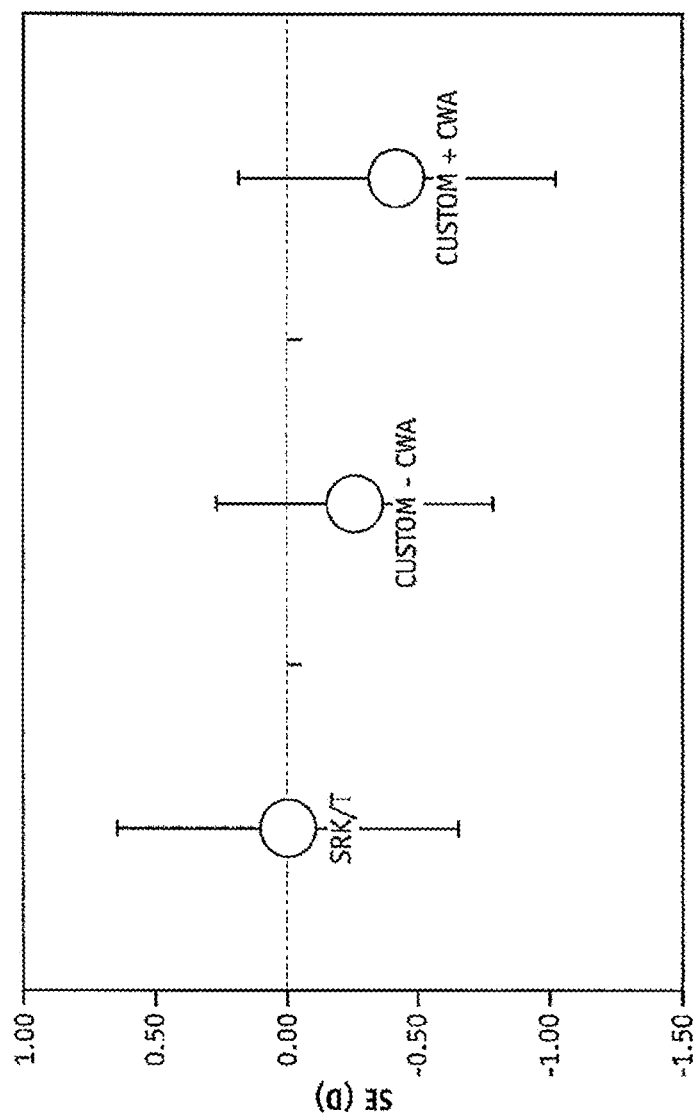
FIG. 2 is a graphical representation comparing the average residual spherical equivalent achieved with ray tracing with and without adding corneal aberrations and current paraxial formulas in 17 normal patients.
Figure 3:
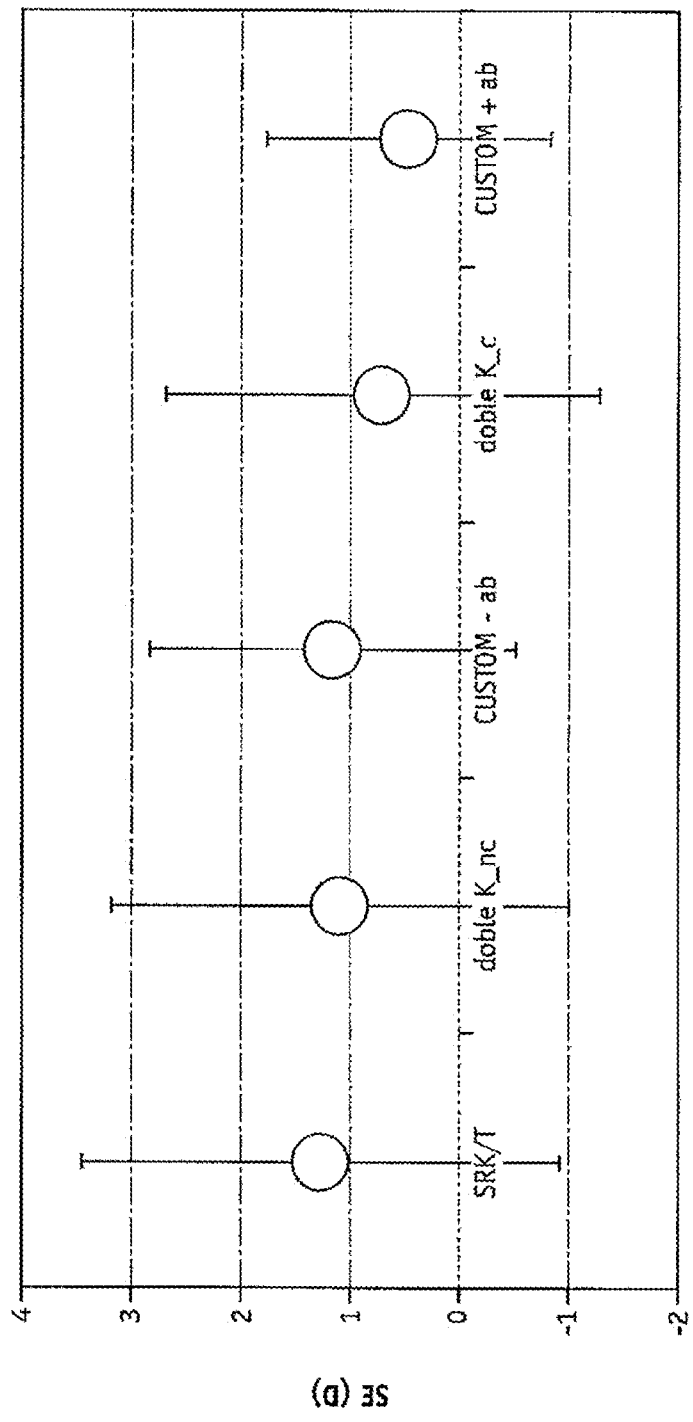
FIG. 3 is a graphical representation comparing the average residual spherical equivalent with ray tracing with and without adding corneal aberrations and current paraxial formulas in 12 postlasik patients.
Figure 4:
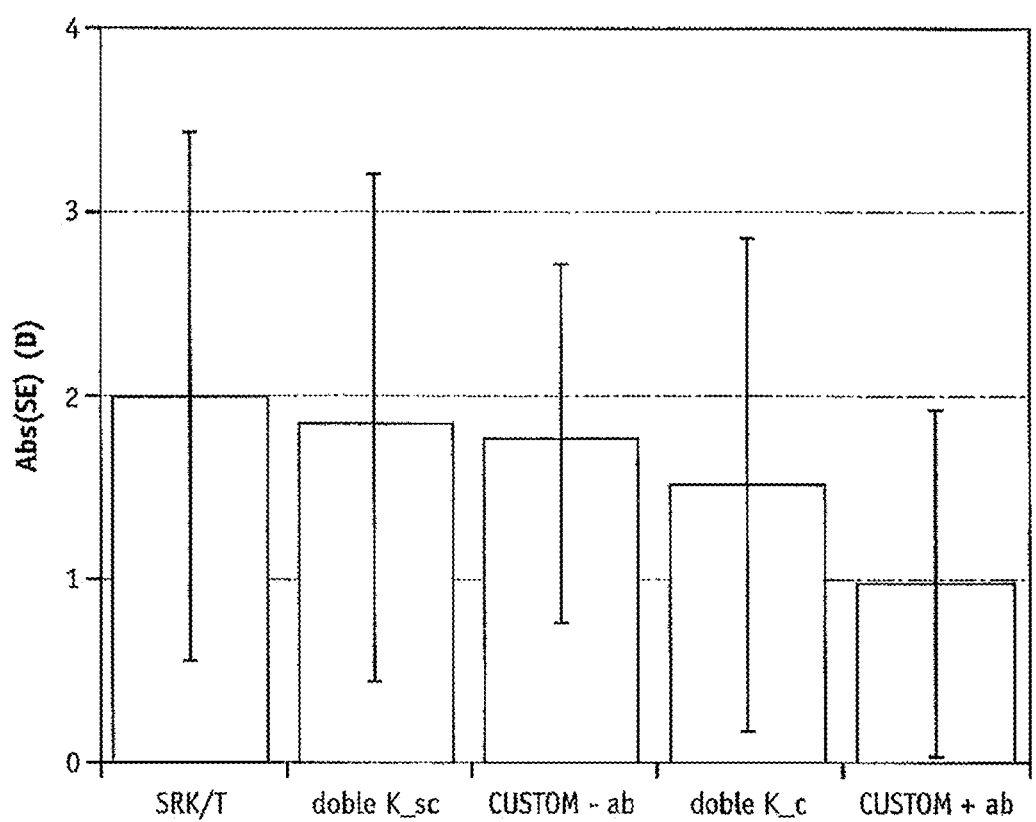
FIG. 4 is a graphical representation comparing the average absolute prediction error achieved with ray tracing with and without adding corneal aberrations and current paraxial formulas in 12 postlasik patients.
Figure 5:
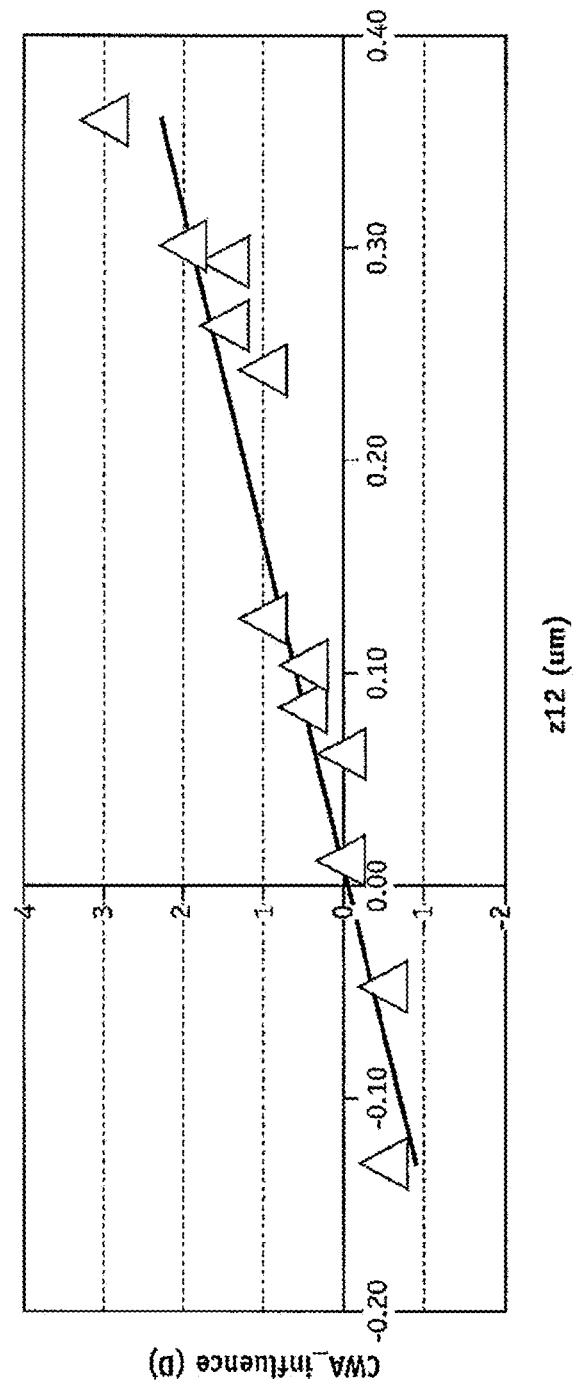
FIG. 5 is a graphical representation comparing difference between ray tracing predictions with and without considering corneal aberrations versus the amount of spherical aberration in postlasik patients.

The present invention includes an intraocular lens, and a system and method of customizing at least one characteristic of an intraocular lens, in accordance with a modified regression that includes a modification for corneal spherical aberration in the modified regression.

The method may include defining a desired postoperative condition of the eye, measuring at least one biometric parameter of an eye, obtaining a corneal spherical aberration of the eye at the desired pupil diameter, applying at least one empirically derived regression calculation, and predictively estimating, in accordance with an output of the at least one empirically derived regression calculation, the at least one characteristic of the intraocular lens to obtain the desired postoperative condition. The empirically derived regression calculation includes at least a product of the corneal spherical aberration with an empirically derived corneal spherical aberration constant, and a mathematical indication of the at least one biometric parameter.

The desired postoperative condition may comprise a postoperative refraction, or the at least one characteristic of the intraocular lens may be an optical power, for example. The at least one biometric parameter may be at least one of axial length, anterior chamber depth and corneal power.

The empirically derived regression calculation may further include a classical regression formula, comprised of the mathematical indication of the at least one biometric parameter, and at least a second constant that is at least one of arithmetically and multiplicatively applied to the classical regression formula. The method may further include selecting an intraocular lens for implantation in accordance with the output of the empirically derived regression calculation.

In addition to aspects of the method of the present invention, the system of the present invention may include a first computing device capable of measuring at least one biometric parameter of an eye, a second computing device capable of measuring and processing or introducing corneal spherical aberration of the eye at different pupil diameters, and a third computing device capable of applying, by at least one computing processor, a modified regression to the at least one biometric parameter and the corneal spherical aberration to output an optimized one of the optical power to obtain a desired postoperative condition. In exemplary embodiments, one of the forms of the modified regression is:

$$P = A*\text{Formula} + D*(\text{corneal spherical aberration}) + E$$

where the constant D is an empirically derived factor across a population of eyes, E is another constant empirically derived result from the regression procedure, and wherein the Formula is a classical regression formula.

The system may further include a feedback input to the third computing device for modifying the modified regression in accordance with the optimized optical power for patients that have already undergone cataract surgery. The Formula may be one selected from Hoffer Q regression, Haigis regression, Holladay1 regression and SRK/T regression.

In addition to the aspects of the method and system of the present invention, an intraocular lens according to the present invention may include a selected optic from a plurality of available optics, wherein the selected optic may be selected based on an optical power that obeys the equation:

$$P = A*\text{Formula} + D*(\text{corneal spherical aberration}) + E,$$

and the lens may further include at least one haptic for physically supporting the selected optic in situ.

Therefore, the present invention provides an apparatus, system and method that provides greater accuracy in predicting optimal IOL power for patients, and in particular, for eyes inside and outside the "average" range.

DETAILED DESCRIPTION OF THE EMBODIMENTS

It is to be understood that the figures and descriptions of the present invention have been simplified to illustrate elements that are relevant for a clear understanding of the present invention, while eliminating, for the purpose of clarity and brevity, many other elements found in typical implantable optic apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The present invention is directed to apparatuses, systems and methods for selecting power for spherical and aspheric intraocular lenses (IOLs) to provide a predetermined refractive outcome for "average" and non-average patients. Aspects of the invention may be understood with reference to FIG. 6, which is a graphical representation of a model eye 20 having cornea 22, iris 24, retina 26, and optical axis 28. IOL 30 is disposed within eye 20, and IOL 30 may include an optic 32 and one or more haptics 34 having distal ends 38. In general, eye 20 may have the dimensional parameters illustrated by the geometry shown, including the axial length (AXL) and the anterior chamber depth (ACD) of eye 20. Other dimensional parameters that may be included in model eye 20, but that are not shown in FIG. 6, include, but are not limited to, the corneal radius (CR), the corneal power (K) and the crystalline lens thickness (LT). Model eye 20 may also include various other parameters, such as, for example, the refractive indices of the various portions of eye 20 and/or IOL 30.

In certain embodiments, distal ends 38 of haptics 34 may be disposed within a plane, defined as the lens haptic plane (LHP). In various embodiments, model eye 20 may include other information indicated by IOL 30, such as, for example, an effective principal plane of optic 32 and/or the location of optic 32 within eye 20.

Figure 6:
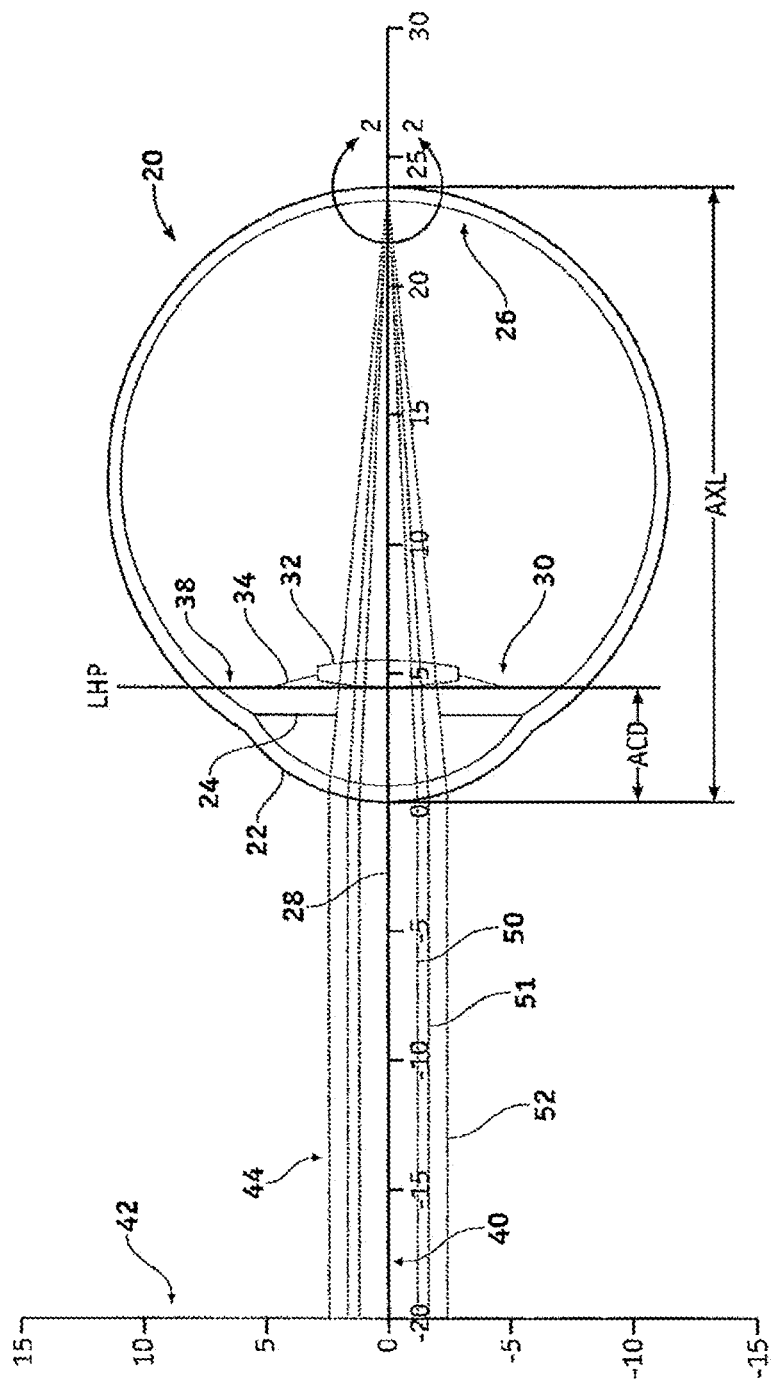
FIG. 6 is a graphical representation of the elements of an eye model used in various embodiments of the present invention.

The illustration of FIG. 6 also indicates a coordinate system having a horizontal axis 40 and a vertical axis 42, shown in units of millimeters. FIG. 6 shows a plurality of rays 44 entering cornea 22 and IOL 30. The plurality of rays 44 comprises a paraxial ray 50 that is disposed near the optical axis 28, and a marginal ray 52 that is disposed near the edge of the opening formed by the iris 24. The plurality of rays 44 additionally comprise of an averaged ray 51 disposed between the paraxial ray 50 and the marginal ray 52, for example, at a height, at the pupil, of 1/{square root over (2)} or ½ times the height of the entrance pupil height. In some embodiments, the eye model may additionally include information regarding an object or source represented by the plurality of rays 44 entering eye 20, such as, for example, the distance of the source or object from eye 20 and/or the extent of the source or object in units of length.

Figure 7:
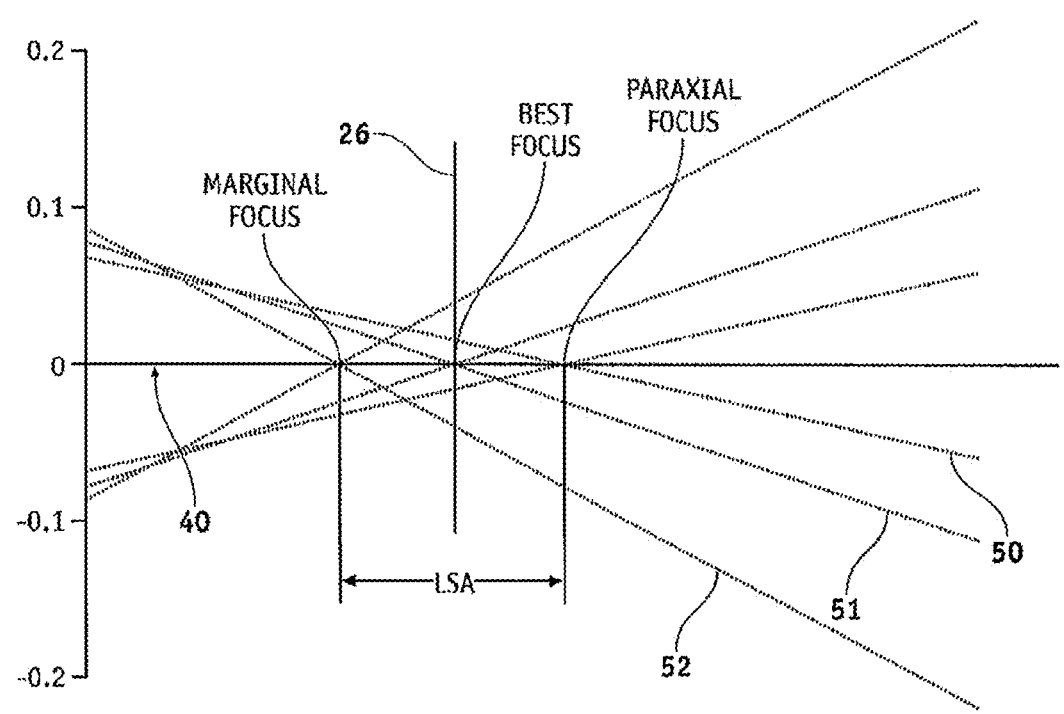
FIG. 7 is a magnified view of the retinal region of the graphical representation shown in FIG. 6.

Referring now to FIG. 7, shown is a magnified view of the region around retina 28, illustrating that rays 50, 51, 52 may come to focus at different points along optical axis 28. These points of focus are labeled as marginal focus, best focus, and paraxial focus. As illustrated, the distance between the marginal focus and the best focus may be used to define a longitudinal spherical aberration (LSA). A LSA may result, for example, when the surfaces of IOL 30 are spherical. Alternatively, one or more of the surfaces of IOL 30 may comprise an aspheric profile that is configured to reduce or eliminate spherical aberrations produced by IOL 30 or by portions of eye 20, such as corneal spherical aberrations (SA) produced by cornea 22.

The present invention may be used to select the characteristics of IOL 30 to be implanted into a subject eye or a class of subject eyes. For example, a class of subject eyes may include subjects of a particular age group or condition (e.g., a class of subjects who have had lasik or a similar procedure). In certain embodiments, measurements from a subject eye, such as the AXL, ACD, CR and/or LT, may be used in conjunction with statistical data and/or an analytical tool to determine the characteristics of IOL 30. The characteristics of the IOL resulting from embodiments of the invention are most particularly the power of the IOL, but may additionally include the thickness of the IOL, the asphericity of the IOL, and/or the location of the IOL within the eye.

The present invention also provides a customizable procedure for predicting the optimum IOL power of a specific IOL 30 for the eye of a particular individual. The apparatus, system and method discussed herein, in formulating the IOL power prediction, take into account biometric parameters of the individual patient and the corneal spherical aberration (SA) of the subject eye. The empirical data discussed herein illustrates that the apparatus, system and method are robust for average patients, as well as for patients having most levels of corneal aberration, including aberrations found in post-lasik patients.

Figure 8:
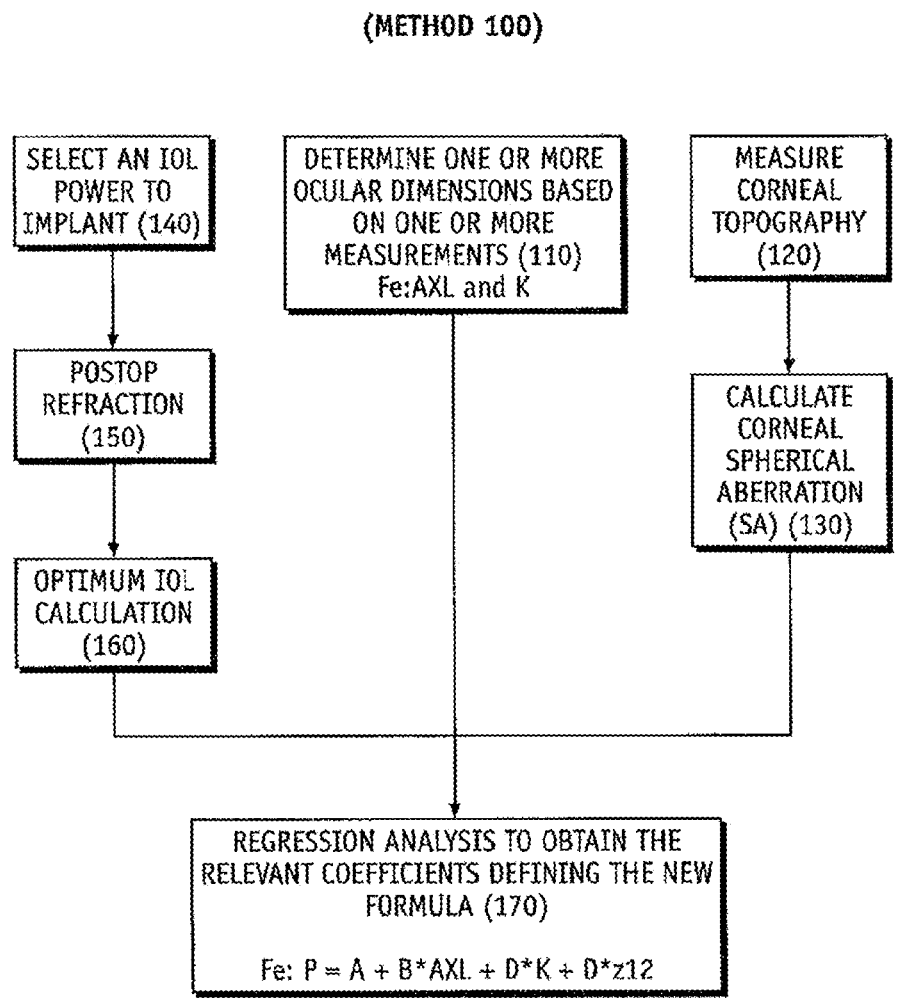
FIG. 8 is a flow chart illustrating a method to develop a regression formula to select an IOL according to exemplary embodiments of the invention.
Figure 9:
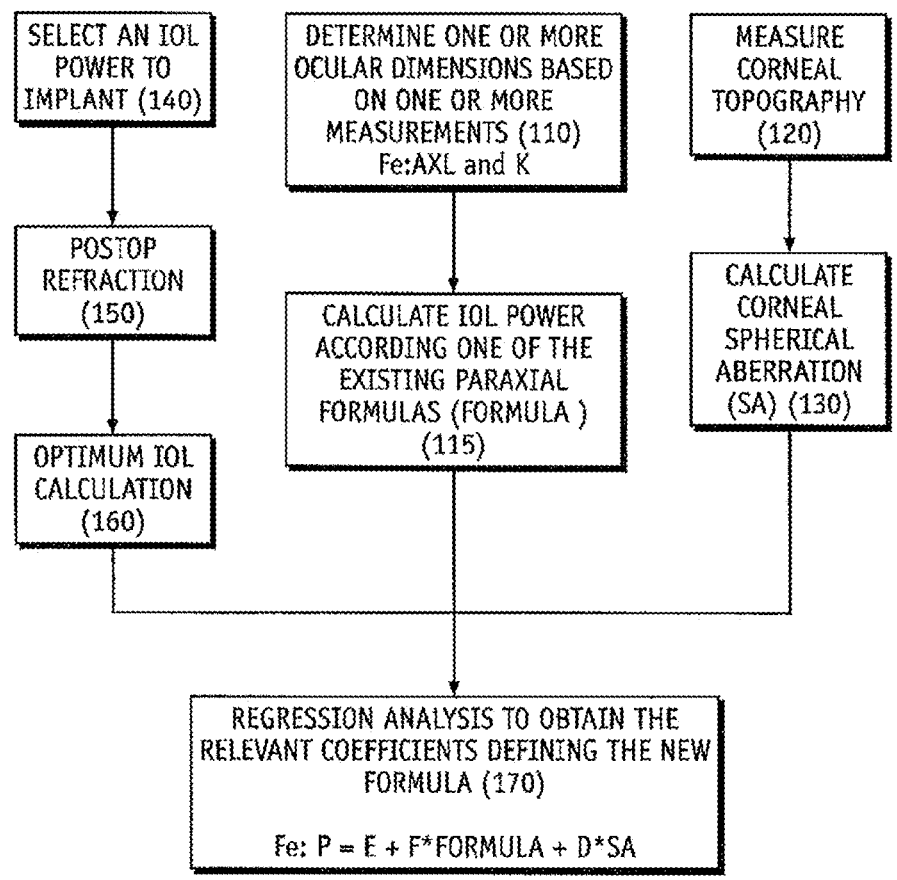
FIG. 9 is a flow chart illustrating an alternative to develop a regression formula to select an IOL using one of the existing paraxial formulas according to exemplary embodiments of the invention.

More particularly, and in accordance with FIGS. 8 and 9, exemplary methods 100/101 of selecting of an IOL may include determining the biometric parameters of the eye, such as the AXL, ACD or K, at step 110. In a preferred embodiment, the number of biometric parameters measured is at least two biometric parameters, or at least 3 biometric parameters, or at least four biometric parameters. The measured biometric parameters may include, for instance, central corneal thickness (CCT) or related corneal pacyhymetry measurements, anterior chamber depth (ACD), pupil diameter (PD), white to white distance (WTW), lens thickness (LT), axial length (AXL), retinal layer thickness (RLT), anterior corneal surface shape, posterior corneal surface shape, anterior lens surface shape, and posterior lens surface shape, lens tilt information and lens position information (including decentration). The relevant biometric parameter may be measured using optical or other instrumental techniques suitable for measuring the relevant biometric parameter and incorporated into a biometric reader 301. Suitable instrumental techniques incorporated into the biometric reader 301 may include one or more of an optical wavefront sensor, a corneal topographer, an optical coherence tomographer, a Scheimpflug Imager, a fluorescence imager, a structured lighting imager, a wavefront tomographer, and an ultrasound imager.

These two methods 100 and 101 can be used to determine a desired postoperative condition, such as a postoperative refraction and/or spherical aberration. The desired refractive outcome may be, for example, improved distance vision and/or near vision, such as providing the subject sufficient visual acuity to eliminate the need for corrective spectacles or contact lenses for near and/or distant vision. Alternatively, the refractive outcome may be to provide sufficient visual acuity such that normal vision is provided without the use of corrective external lenses, or by the use of corrective spectacles or contact lenses having a correction of less than about 3 diopters, preferably less than about 2 diopters, or more preferably less than about 1 diopter. Most particularly, the present invention has, as a desired refractive outcome, to obtain the desired postoperative outcome with the predicted IOL power.

Both methods 100 and 101 further include at step 130, a representation of the corneal topography obtained at step 120, in the form of at least one corneal aberration. Corneal topography may be measured by, for example, optical coherence tomography or by other corneal topography methods. These corneal aberrations can be obtained by the internal process of the apparatus used or by the external process from corneal elevations achieved by corneal topographers. It may also be obtained using an analytical tool, such as using established ray tracing procedures. As used herein, a ray tracing procedure is a procedure that simulates the light propagation and refraction, by means of an exact solution of Snell's law, for all rays passing through an optical system. Those skilled in the art will appreciate that, for example, a Zemax optical design software simulation may be employed in order to provide the ray tracing modeling discussed herein.

In accordance with step 130, the SA may be obtained pursuant to the light level, such as at the 4 mm pupil. The desired light level may simulate, for example, mesopic light (dusk). The pupil size at dusk is typically about 4 mm, but may vary between at least about 2 mm to about 6 mm or more. The mesopic light pupil size may be selected, by way of example, in part because the about 4 mm pupil is a realistic pupil for cataract patients and allows for the introduction of aberrations that are omitted in paraxial optics (herein defined as the study of optics related to small angles, and small apertures).

From these results, at step 140 the IOL power to implant for the patient will be calculated following the standard procedures in cataract surgery. At step 160 the optimum IOL power is back calculated from each patient from knowledge of the postoperative refraction, obtained at step 150. Once this is calculated in the IOL plane, this will be added to the implanted IOL power thus defining the optimum IOL power for the patient.

Using the data gained at step 160, a multiple regression analysis may be performed across several subjects in order to establish the final formula to use, based on pre-operative data and corneal spherical aberration, to predict the optimum IOL characteristics, such as the optimum IOL power, at step 170.

The main difference between method 100 (FIG. 8) and 101 (FIG. 9) is the nature of the regression data. In method 100, optimization is based directly on the constants, which weight each of the input parameters obtained at step 110, as well as the corneal spherical aberration at step 130. On the other hand, corneal spherical aberration is also considered as a parameter in method 101. In method 101, the other parameter is the IOL power calculated using preoperative data from one of the current paraxial optic formulas calculated at step 115.

In both methods, the final regression allows for improved prediction of IOL characteristics, such as IOL power, for subsequent average and non-average subjects at step 170. Because of the regression nature of these formulas, they can be continuously updated by the addition of new patients, personalizing in this way the different constants involved in the calculation.

Figure 10:
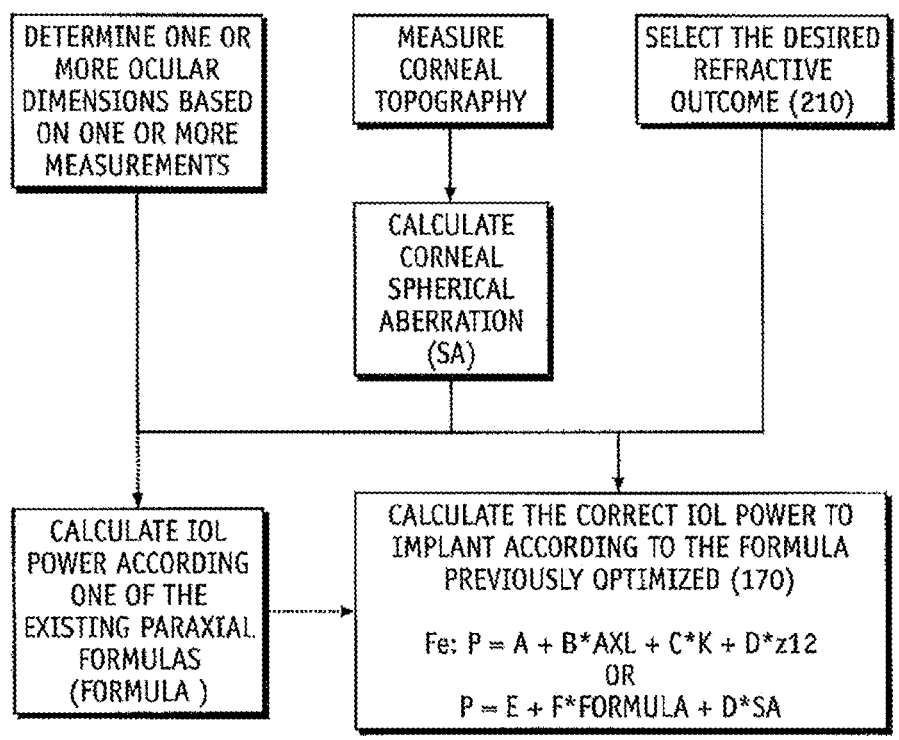
FIG. 10 is a flow chart illustrating a method of selecting an IOL according to exemplary embodiments of the invention.

Once the formula has been established, the procedure 200, described in FIG. 10, can be used to predict a desired postoperative condition in a different population than that from which formula 170 had been obtained, such as a postoperative refraction and/or spherical aberration, at step 210 by previous knowledge of biometric parameters included in the formula (directly as inputs if method 100 is applied to develop procedure 200 or, in the case of method 101, the input will be from one of the current paraxial formulas used to compute the IOL power) as well as corneal spherical aberration and the selected refractive stage after the surgery.

Methods of predicting refractive outcomes, such as refractive outcomes correcting "average" or "normal" SA in a patient group, based on IOL characteristics is well understood, and embodiments of such analyses are detailed in, for example, U.S. Pat. No. 6,609,793, which is herein incorporated by reference. More particularly, corneas of the normal population, which have historically been the subject of regression analysis at step 170, show on average positive spherical aberration. However, methods 100 or 101 of the present invention, which use a customized regression from step 170, allow for optimal IOL characteristic prediction for IOLs to treat corneas having all types of corneal SA including providing optimal IOL characteristic prediction for all types of spherical or aspheric IOLs. For example, patients who had lasik to correct myopia may have an increased value of positive spherical aberration with respect to the average normal population, while those who had corneal refractive surgery to correct hyperopia may present minor spherical aberration as compared to the average. Methods 100 or 101 provide optimal IOL characteristics, such as optimal IOL power, based on the customized regression from step 170.

The interaction between defocus, related to IOL power and spherical aberration has been reported (Applegate R. A., Marsack J. D., Ramos R., Edwin E. J. Sarver, 'Interaction between aberrations to improve or reduce visual performance', *J Cataract Refract Surg* 2003; 29:1487-1495). Thus, modifying IOL power in accordance with spherical aberration can improve visual performance. The inclusion in the regression of an additional constant, herein referred to as constant D, obtained in the regression of step 170 accounts for the variation of corneal SA parameter for individuals.

In addition, it has been clinically shown, based on a statistically significant population, that there is a nominal change of 0.7 diopters or more in the A constant in the SRK/T regression analysis as between a spherical IOL having a positive spherical aberration, and an aspherical IOL having a negative spherical aberration. Because the characteristics of the exemplary IOLs were the same in each case, with the exception of the spherical aberration (SA) parameter, it may be inferred from these clinical findings that the change in the A constant for a regression analysis is due to the SA.

The cornea may present SA in different amounts. Thus, for example, the optimal IOL power calculated by the regression from step 170 may comprise constant D to minimize the spherical equivalent (SE) of the eye. Minimization of the SE is particularly applicable in patients with less than about 1 diopter of corneal astigmatism, where visual performance is still good without the need of a toric IOL. This is an advantageous modeling approach, in part because the SE does not appreciably change due to, for example, the incision in a cataract surgery. On the contrary, corneal astigmatism and power may change pursuant to cataract surgery.

This procedure can be also extended to toric IOL power calculations. The spherical equivalent of an IOL can be calculated following a similar procedure as 200. The toric IOL power may then be obtained by the difference between the paraxial calculation for the flat and steep meridian. Further optimization may be possible considering corneal spherical aberration or other corneal aberrations in those meridians to improve the cylinder prediction as well as the spherical equivalent prediction.

Methods 100 or 101 thus account for the non-constant nature of SA in a broader population of surgical subjects, based on the applicability of methods 100 or 101 to "average" eyes, as that term is defined above, and to non-average eyes, such as eyes having significant SA. For a more detailed discussion of the variation of SA across a broad candidate population, see G. H. H. Beiko, et al., "Distribution of Corneal Spherical Aberration in a Comprehensive Ophthalmology Practice, and Whether Keratometry Can Predict Aberration Values," *J. Cataract Refract. Surg., vol. 33* (2007), pp. 848-858.

More particularly, the present invention improves the prediction of IOL characteristics, and specifically IOL power, across the broad population that includes average and non-average eyes through the application, at step 170 of method 100 or 101. The final regression from step 170 improves predictive accuracy by introducing an additional regression parameter, namely constant D, to account for SA. More particularly, the modification to known regression approaches may be made to improve predictive accuracy, particularly in non-average subjects, as seen in the following example of method 101:

$$P = \text{Formula} + D*SA \quad \text{[EQUATION 1]}$$

where P is IOL power, and Formula is a regression formula known in the current art.

The customized regression from step 170, as illustrated in EQUATION 1, includes a constant obtained empirically for association with the customized variable for corneal SA. By way of example, the present inventors have empirically obtained a variety of constants D for inclusion in different ones of the classical regression formulae, and exemplary ones of these constants D are discussed further below in EQUATIONS 4-8.

Of course, those skilled in the pertinent arts will appreciate, in light of the discussion herein, that an adjustment constant or constants may also be applied to the Formula prior to or in conjunction with the modification made to account for the SA. That is, the present invention may calculate the recommended IOL power as disclosed in the following example of method 101:

$$P = E + F*\text{Formula} + D*SA \quad \text{[EQUATION 2]}$$

where E may be zero or non-zero, and where F is non-zero.

As was described in method 100, another possible implementation of this idea is to consider the classical SRK regression model and then adjust all the constants involved in addition to those related to SA as follows:

$$P = A - B*AXL - C*K + D*SA \quad \text{[EQUATION 3]}$$

where D is the aforementioned constant applied to the SA, and A, B and C are the remaining constants which may also be optimized in order to improve the IOL power prediction.

In order to show the feasibility of taking into account, for example, the z12 Zernike term (SA) in IOL power calculations and the implementation of the invention disclosed herein, the present inventors have empirically derived a SA adjustment from a sampling of 97 average subjects using modifications to the SRK following method 100 (SRK optimized+z12) and SRK/T regressions (SRK/T modified+z12), following method 101, being the SRK/T uses a paraxial formula, and have empirically derived a SA adjustment from a sampling of 29 non-average, postlasik subjects using modifications to the SRK following method 100 (SRK optimized+z12) and for the SRK/T, Haigis, Holladay 1 and Hoffer Q formulae according method 101 (referred to be SRK/T+z12, Haigis+z12, Holladay 1+z12 and Hoffer Q+z12 respectively). Of course, those skilled in the art will appreciate that any known regression may be modified, in accordance with the present invention, using empirical data gained from any statistically significant number of subjects, and thus the present invention is not limited to the regressions and subjects or numbers of patients discussed with particularity herein.

Figure 11:
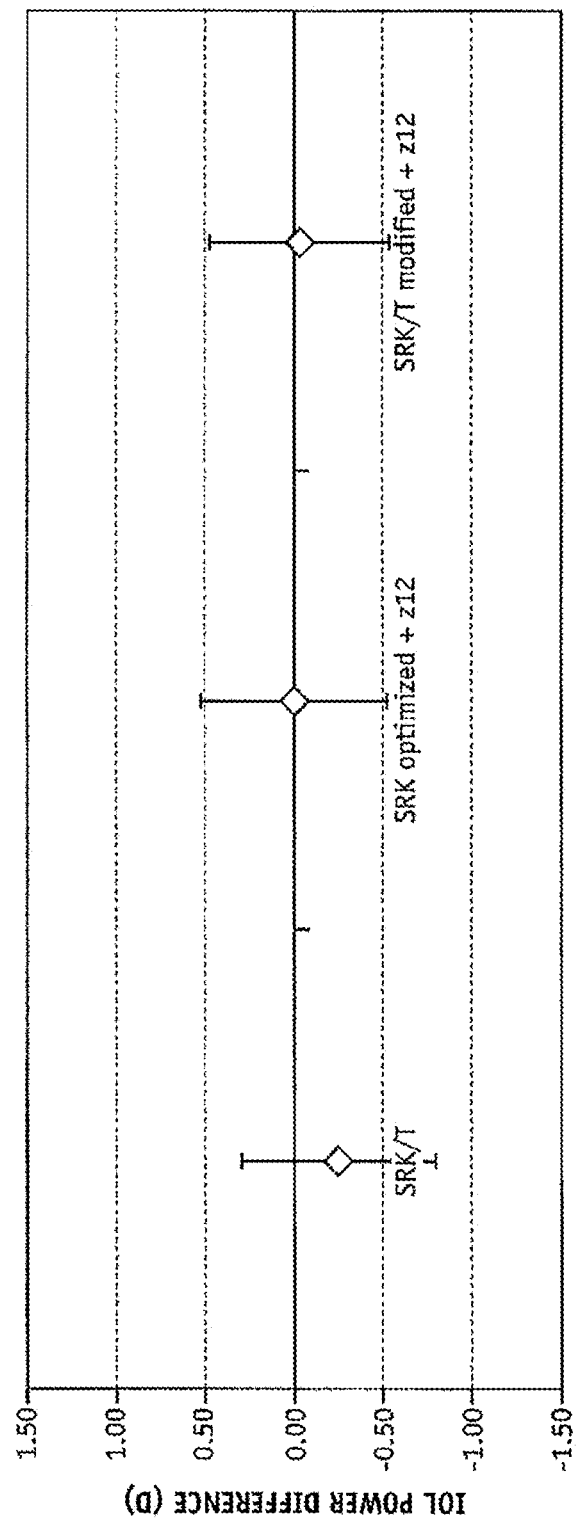
FIG. 11 is a graph comparing the residual error in IOL power calculation between the current state of art and these formulas developed used the method present here for normal patients.
Figure 12:
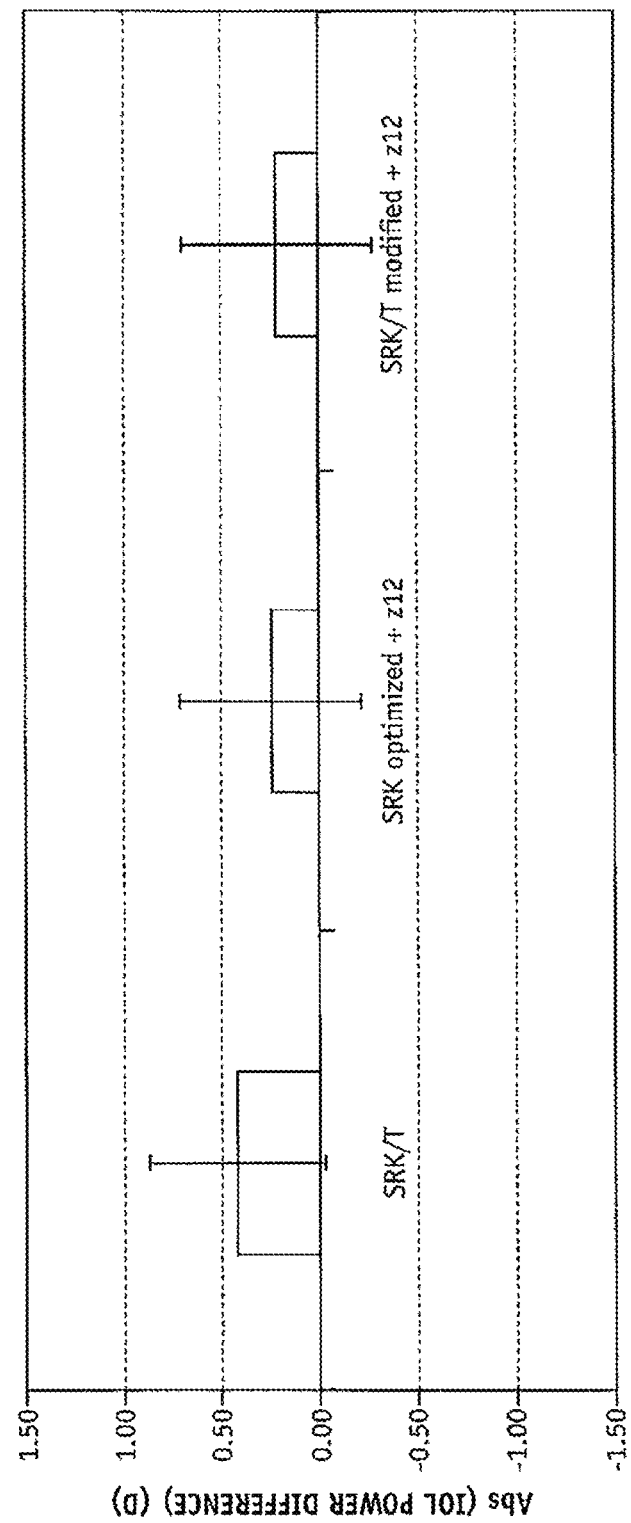
FIG. 12 is a graph comparing the absolute residual error in IOL power calculation between the current state of art and these formulas developed used the method present here for normal patients.
Figure 13:
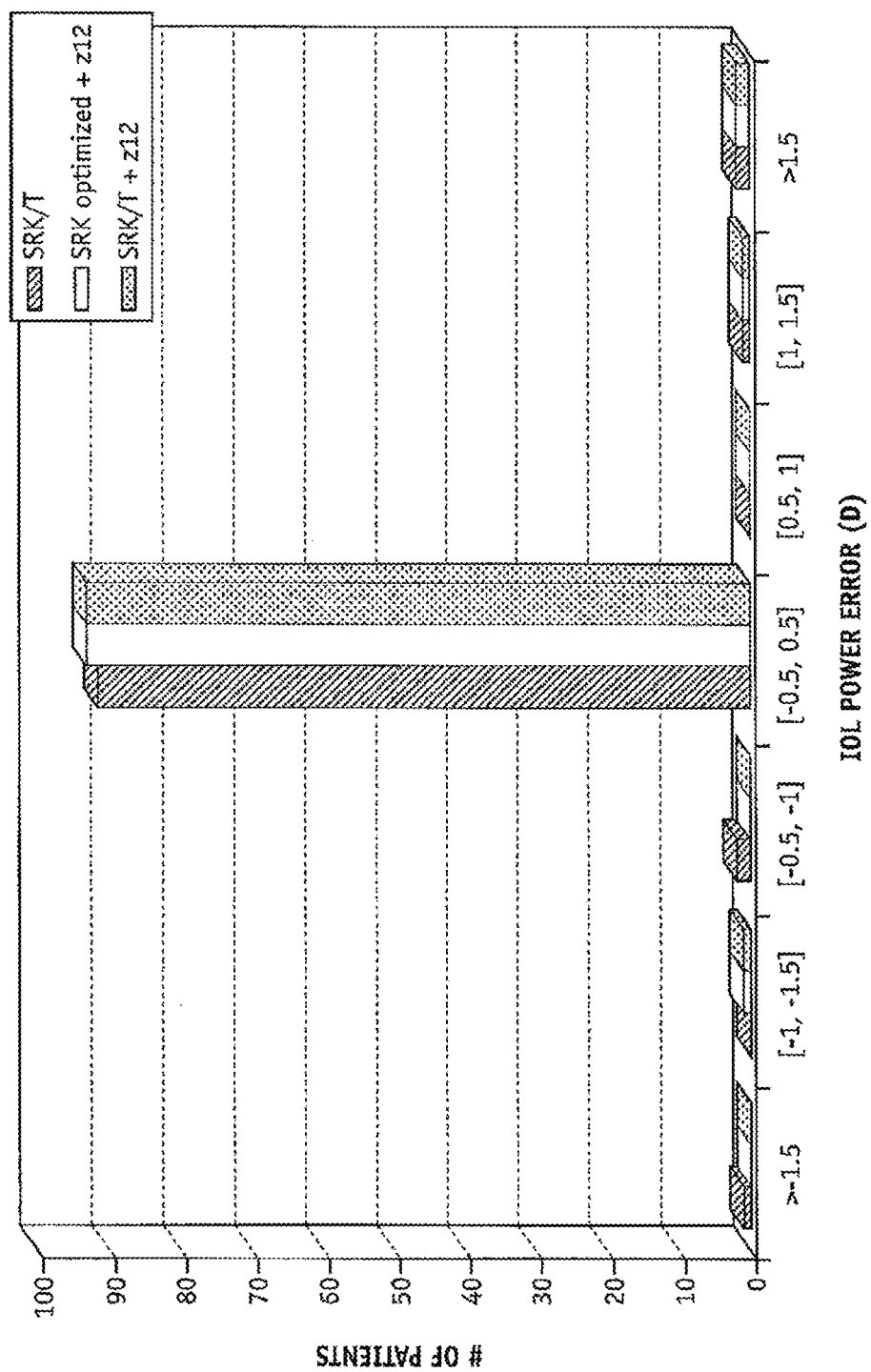
FIG. 13 shows the number of normal patients whose prediction error using different approaches is inside of different ranges.

More specifically, FIGS. 11 and 12 illustrate the comparison between the difference with respect to optimum IOL power and those calculated for the data obtained from the 97 average patients referenced above, using the SRK/T+z12 formula and the SRK optimized+z12 formula. In the illustration, the optimum IOL power was known for each patient following implantation, and was compared to the predicted outcome of the SRK/T+z12 formula and/or the SRK optimized+z12 formula (with SA in the OSA convention and at about 4 mm pupil). FIGS. 11 and 12 show a slight improvement in the error, in Diopters, in the IOL power predicted both by the SRK/T+z12 or SRK optimized+z12 formula as compared to the SRK/T formula, for patients having SA in the "average" range. FIG. 13 illustrates this slight predictive improvement in the error for the prediction using both the SRK/T+z12 or SRK optimized+z12 formula as compared to the classical SRK/T approach.

For non-average subjects, it is well known that the same formulas as used for normal patients do not provide good results. Varying solutions to improve the calculations for these types of patients have been proposed. These solutions include: calculating the IOL power based on the corneal power prior to, for example, lasik surgery; applying the "Double K" method; and the aforementioned and other retrospective regression analyses.

Various studies have shown that, of the aforementioned solutions, those based on pre-lasik data are less accurate than regression methods correcting corneal power (see, e.g. Wang L, Hill W E, Koch D D, 'Evaluation of intraocular lens power prediction methods using the American Society of Cataract and Refractive Surgeons Post-Keratorefractive Intraocular Lens Power Calculator', *J Cataract Refract Surg.* 2010 September; 36(9):1466-73, which is incorporated herein by reference as if set forth in its entirety). Thus, method 101 of the present invention, using the data related to the 29 myopic postlasik patients referenced above (including the IOL power necessary for an emmetropic outcome and the SA, as calculated from measured corneal topography, with no corneal power corrections and using no pre-lasik data), was applied to calculate the IOL power, including at step 115 the SRK/T, Hoffer Q, Holladay 1, and Haigis formulas, which results were used in addition to corneal spherical aberration to generate the corresponding modified regression formulas at step 170. In addition, method 100 was applied in the same subjects in order to develop a SRK optimized+z12 regression.

Figure 14:
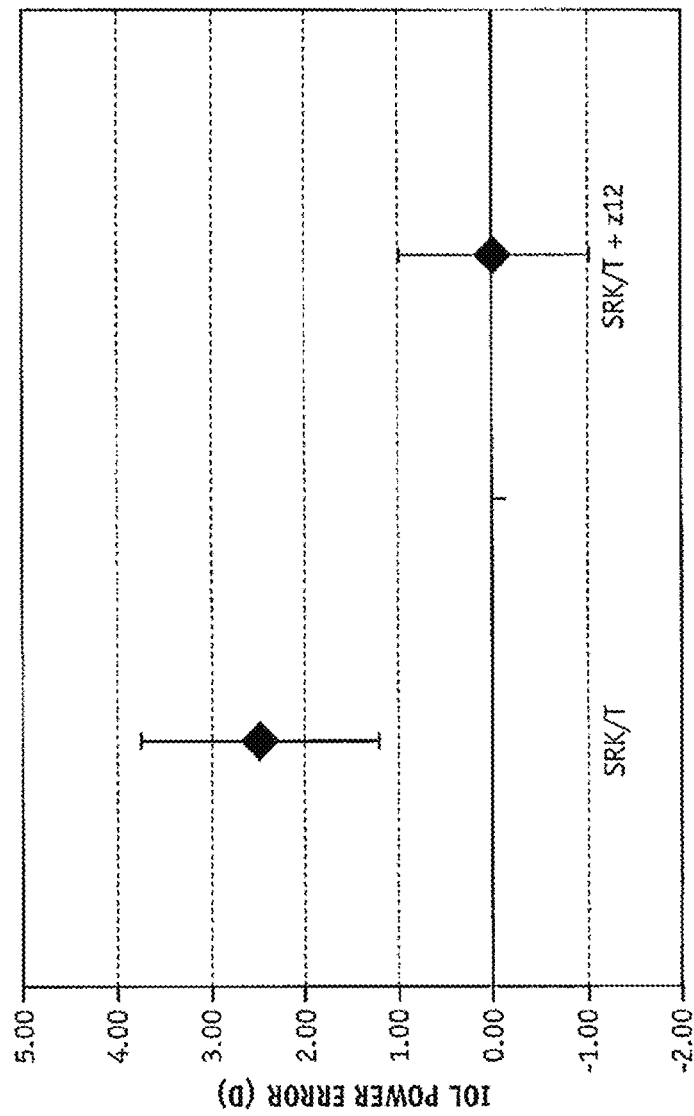
FIG. 14 shows the IOL power prediction error both for the SRK/T formula and the SRK/T considering corneal spherical aberration for postlasik patients.
Figure 15:
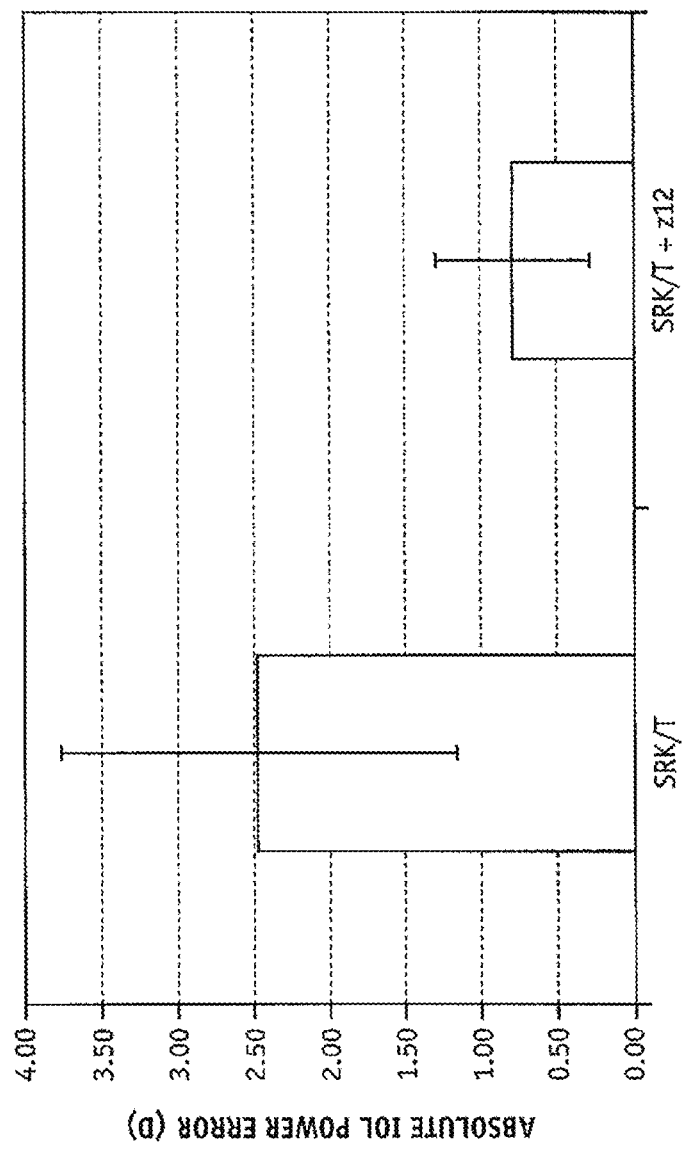
FIG. 15 shows the absolute IOL power prediction error both for the SRK/T formula and the SRK/T considering corneal spherical aberration for postlasik patients.

For example, FIGS. 14 and 15 illustrate a comparison of the error of the predicted IOL power, for the referenced 29 non-average patients, for the SRK/T and SRK/T+z12 formulae. As shown, the inclusion of the adjustment for the SA decreases the error in the predicted IOL power. More particularly, the SRK/T+z12 formula indicated at step 170 of method 101 is:

$$P = 1.70056 + 0.955562*SRK/T + 9.804702*z12. \quad \text{[EQUATION 4]}$$

Figure 16:
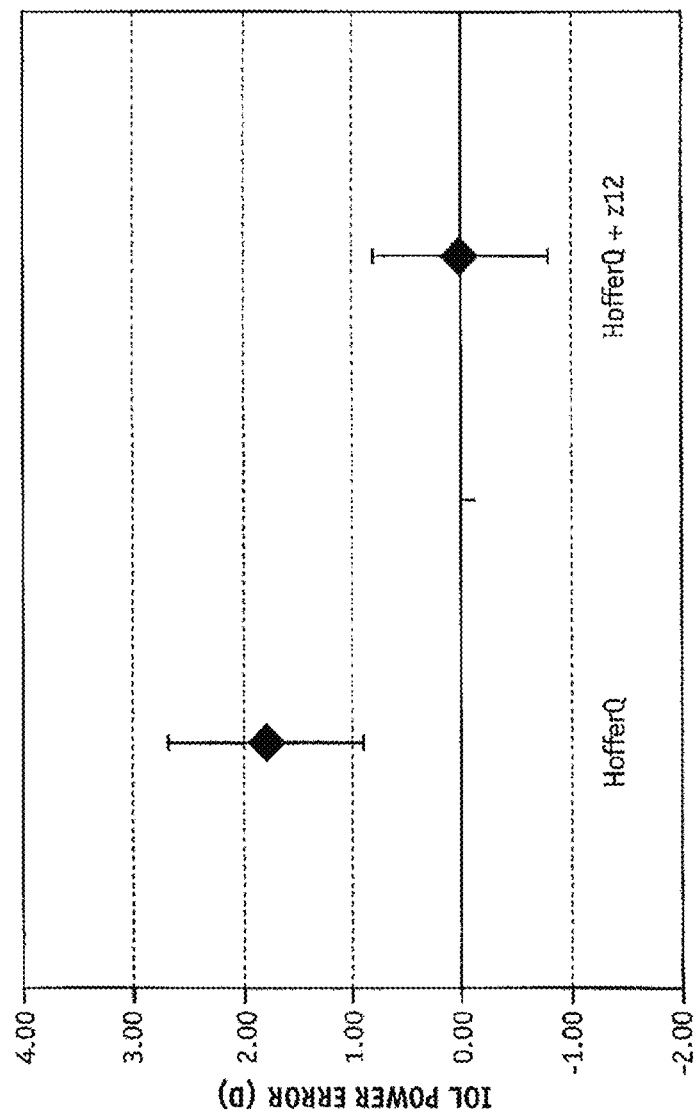
FIG. 16 shows the IOL power prediction error both for the HofferQ formula and the HofferQ considering corneal spherical aberration for postlasik patients.
Figure 17:
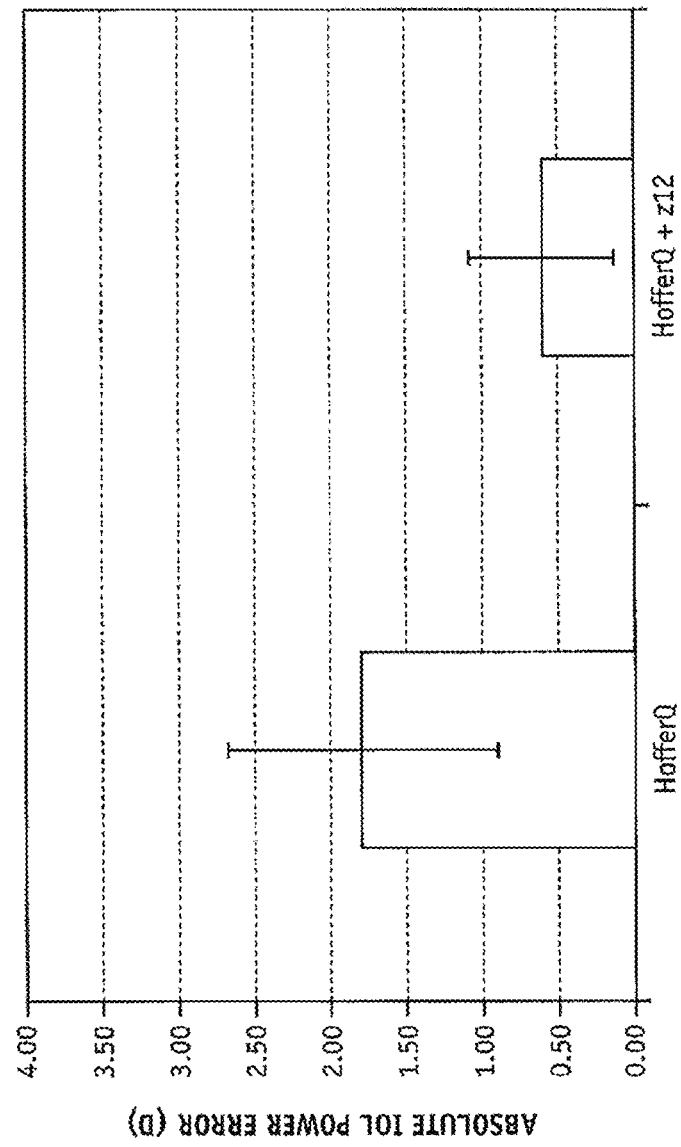
FIG. 17 shows the absolute IOL power prediction error both for the HofferQ formula and the HofferQ considering corneal spherical aberration for postlasik patients.

Further, for example, FIGS. 16 and 17 illustrate a comparison of the error of the predicted IOL power, for the referenced 29 non-average patients, for the Hoffer Q and Hoffer Q+z12 formulae. As shown, the inclusion of the adjustment for the SA substantially decreases the error in the predicted IOL power. More particularly, the Hoffer Q+z12 formula indicated at step 170 of method 101 is:

$$P=2.057938+0.944393*HofferQ+4.671033*z12. \quad [\text{EQUATION 5}]$$

Figure 18:
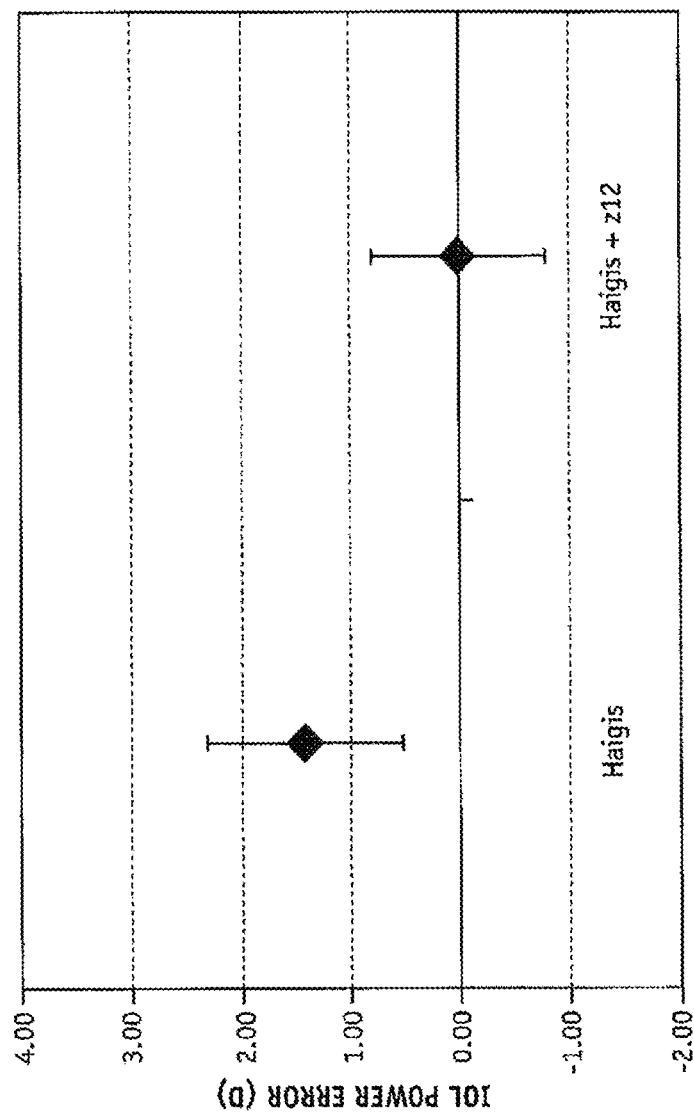
FIG. 18 shows the IOL power prediction error both for the Haigis formula and the Haigis considering corneal spherical aberration for postlasik patients.
Figure 19:
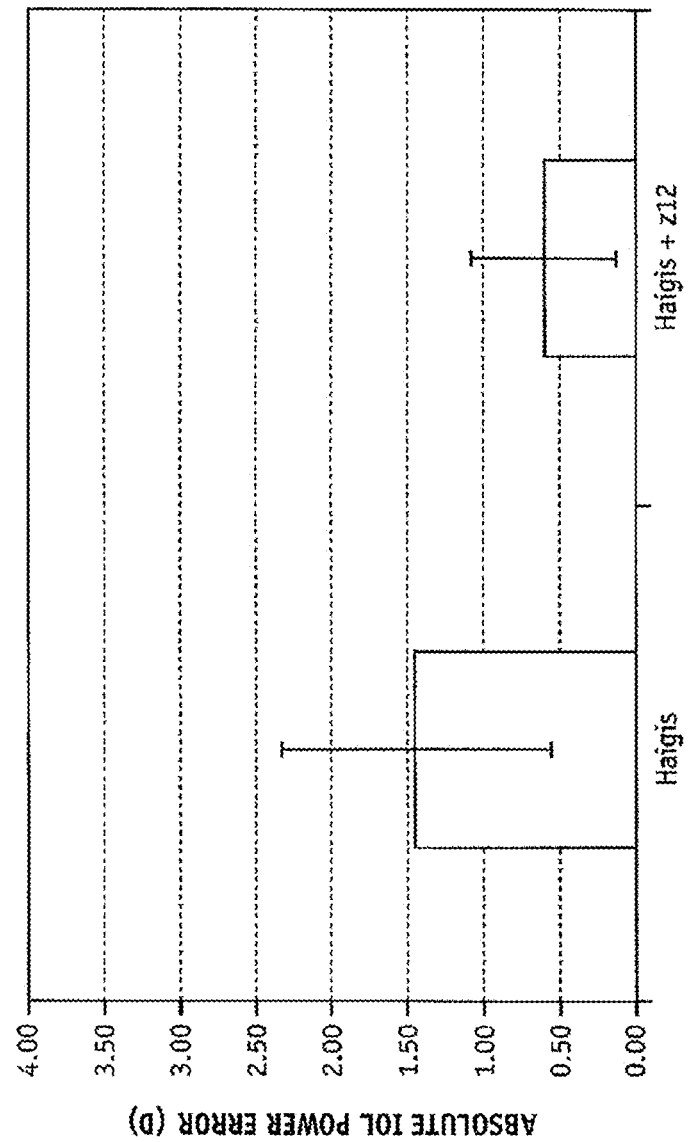
FIG. 19 shows the absolute IOL power prediction error both for the Haigis formula and the Haigis considering corneal spherical aberration for postlasik patients.

By way of additional non-limiting example, FIGS. 18 and 19 illustrate a comparison of the error of the predicted IOL power, for the referenced 29 non-average patients, for the Haigis and Haigis+z12 formulae. As shown, the inclusion of the adjustment for the SA substantially decreases the error in the predicted IOL power. More particularly, the Haigis+z12 formula indicated at step 170 of method 101 is:

$$P=1.10511+0.986052*Haigis+3.792270*z12. \quad [\text{EQUATION 6}]$$

Figure 20:
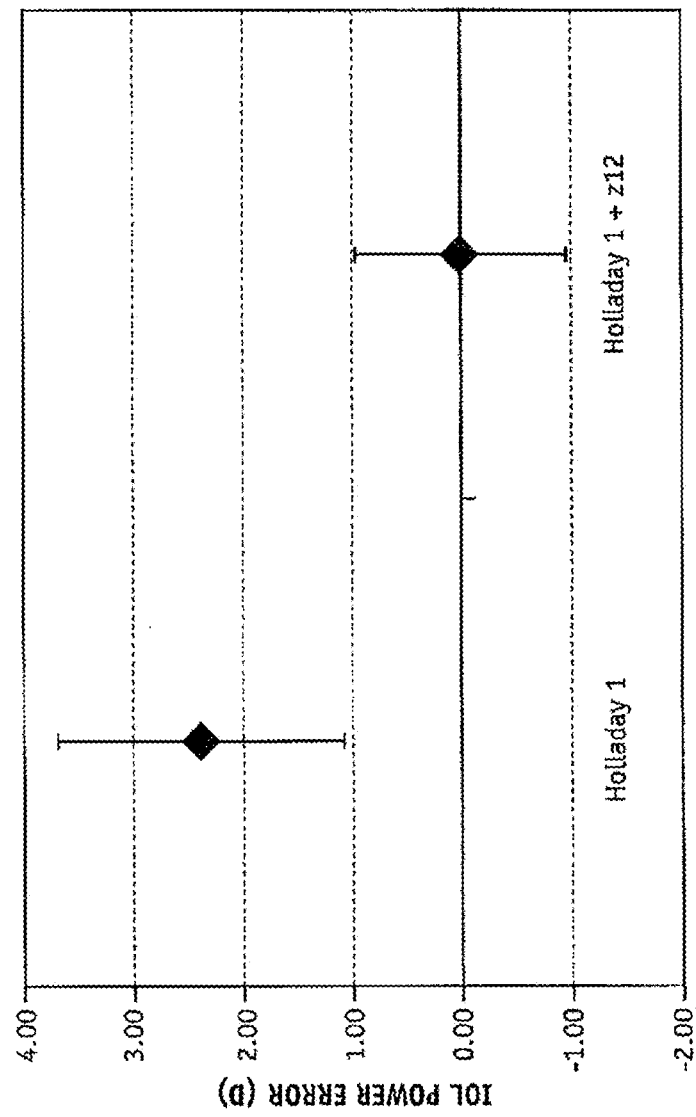
FIG. 20 shows the IOL power prediction error both for the Holladay1 formula and the Holladay1 considering corneal spherical aberration for postlasik patients.
Figure 21:
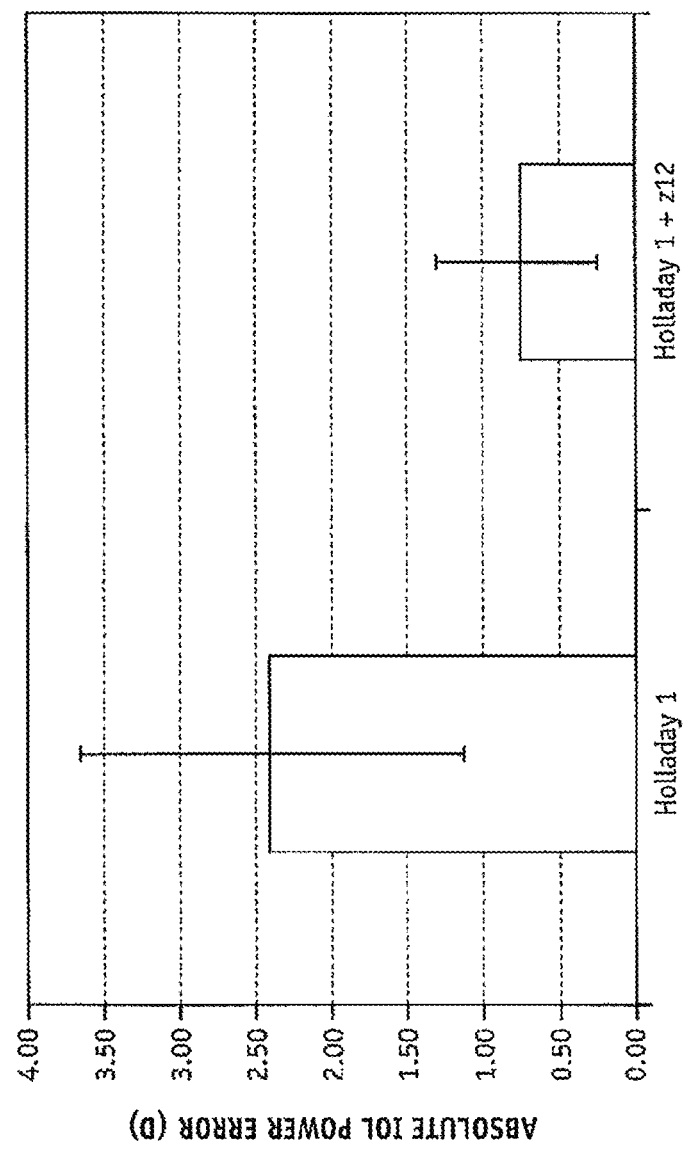
FIG. 21 shows the absolute IOL power prediction error both for the Holladay1 formula and the Holladay1 considering corneal spherical aberration for postlasik patients.

Yet further, FIGS. 20 and 21 illustrate a comparison of the error of the predicted IOL power, for the referenced 29 non-average patients, for the Holladay 1 and Holladay 1+z12 formulae. As shown, the inclusion of the adjustment for the SA substantially decreases the error in the predicted IOL power. More particularly, the Holladay 1+z12 formula indicated at step 170 of method 101 is:

$$P=2.787859+0.888706*Holladay+9.695131*z12. \quad [\text{EQUATION 7}]$$

For each of the aforementioned regressions, the effect of the modification for SA is statistically significant. Further, those skilled in the art will appreciate that the constants employed in EQUATIONS 4-7 are exemplary only, and thus may be modified yet still fall within the scope of the present invention. Thereby, modification to the exemplary constants respectively provided for z12 may be necessary.

In addition, method 100 was applied and a SRK modified+z12 formula was obtained at step 170, that is:

$$P=140.8232-2.651*AXL-1.3102*K+4.767704*z12. \quad [\text{EQUATION 8}]$$

P represents the IOL power to implant. AXL represents the axial length measured prior to the surgery. K represents the corneal power also measured in the cataract preoperative stage. z12 represents the aforementioned corneal spherical aberration.

As referenced above, the Double K method with the Wang, Koch, Maloney correction or the Haigis L formula are manners of assessing IOL power for postlasik patients that are frequently employed in the current art.

Figure 22:
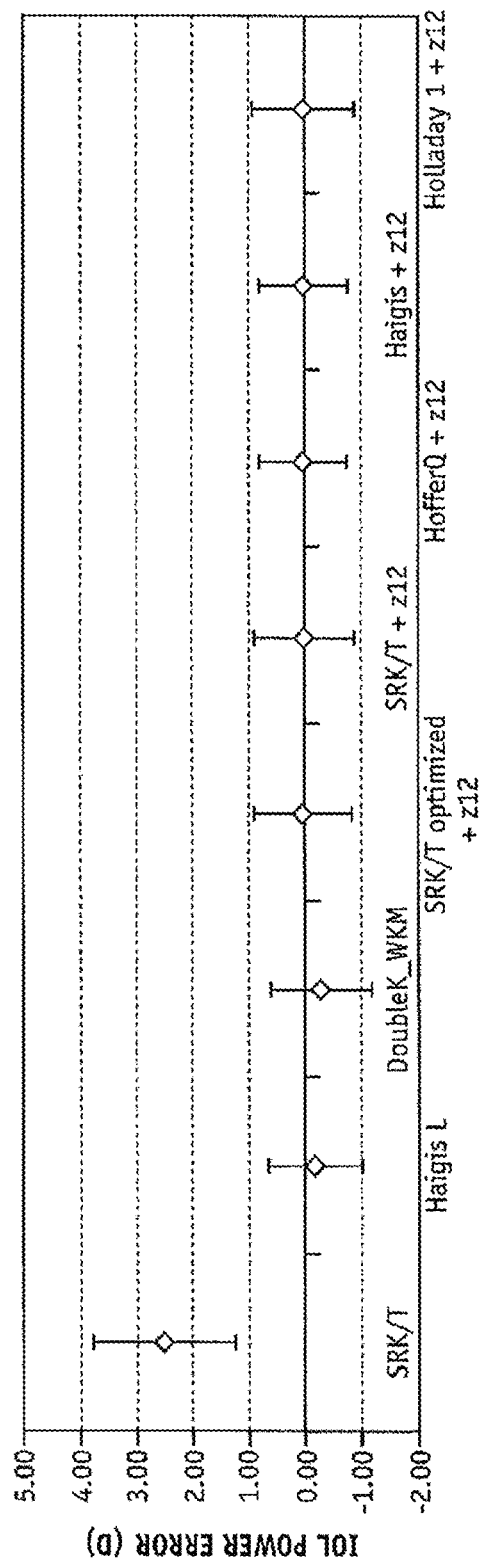
FIG. 22 shows the IOL power prediction error for different paraxial formulas considering corneal spherical aberration in comparison with the current state of art for postlasik patients.
Figure 23:
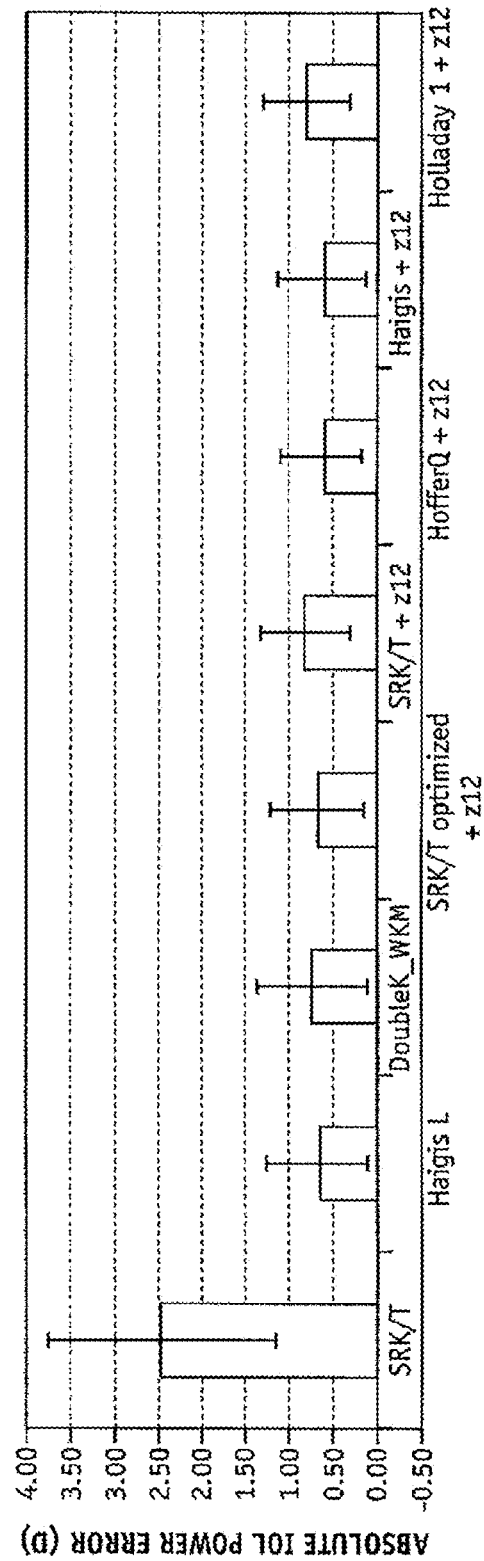
FIG. 23 shows the absolute IOL power prediction error for different paraxial formulas considering corneal spherical aberration in comparison with the current state of art for postlasik patients.

FIGS. 22-23 graphically illustrate the improvement in the required value minus the predicted value over the current state of the art, represented by the double K method with the Wang, Koch and Maloney (DoubleK_WKM) correction as well as the HagisL formula, provided by the present invention, particularly for the HofferQ+z12 and Haigis+z12 approaches. More particularly, Table 1 illustrates that the HofferQ+z12 and Haigis+z12 retrieved less error, less absolute error, and had an improved standard deviation as compared to the current state of art.

TABLE 1

|  | error | desvest | abs(error) | desvest |
|---|---|---|---|---|
| Haigis L | −0.22 | 0.86 | 0.66 | 0.58 |
| DoubleK_LW | −0.33 | 0.92 | 0.73 | 0.64 |
| SRK optimized + z12 | 0.00 | 0.88 | 0.68 | 0.55 |
| SRK/T + z12 | 0.00 | 0.97 | 0.81 | 0.50 |
| HofferQ + z12 | 0.00 | 0.79 | 0.62 | 0.48 |

TABLE 1-continued

|  | error | desvest | abs(error) | desvest |
|---|---|---|---|---|
| Haigis + z12 | 0.00 | 0.80 | 0.61 | 0.50 |
| Holladay1 + z12 | 0.00 | 0.95 | 0.79 | 0.51 |

Figure 24:
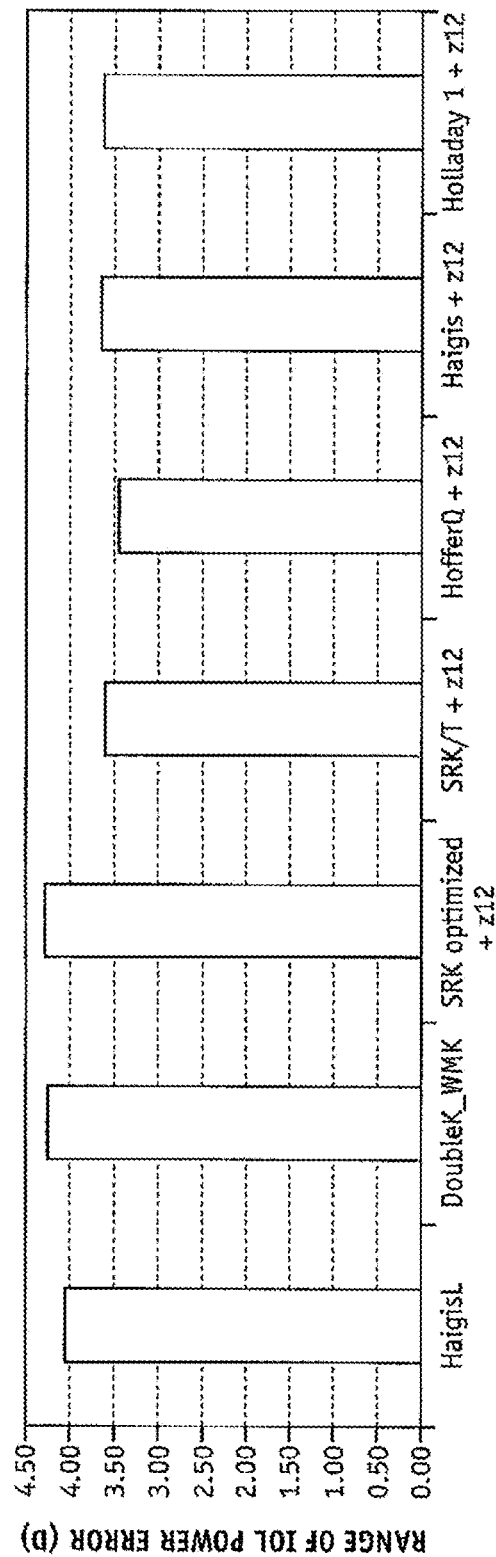
FIG. 24 shows the maximum range of IOL power prediction error for different paraxial formulas considering corneal spherical aberration in comparison with the current state of art for postlasik patients.

FIG. 24 shows the maximum range of error, defined as the most positive error minus the most negative error retrieved by each of the formulas for those patients included in the study. It discloses that, especially for those formulas retrieved by method 101, the range of error is reduced between 0.4 and 0.8 D, thus making the calculated IOL power much more predictable. In the case of the SRK optimized+z12, the range of error is similar to those formulas that represent the current state of art.

Figure 25:
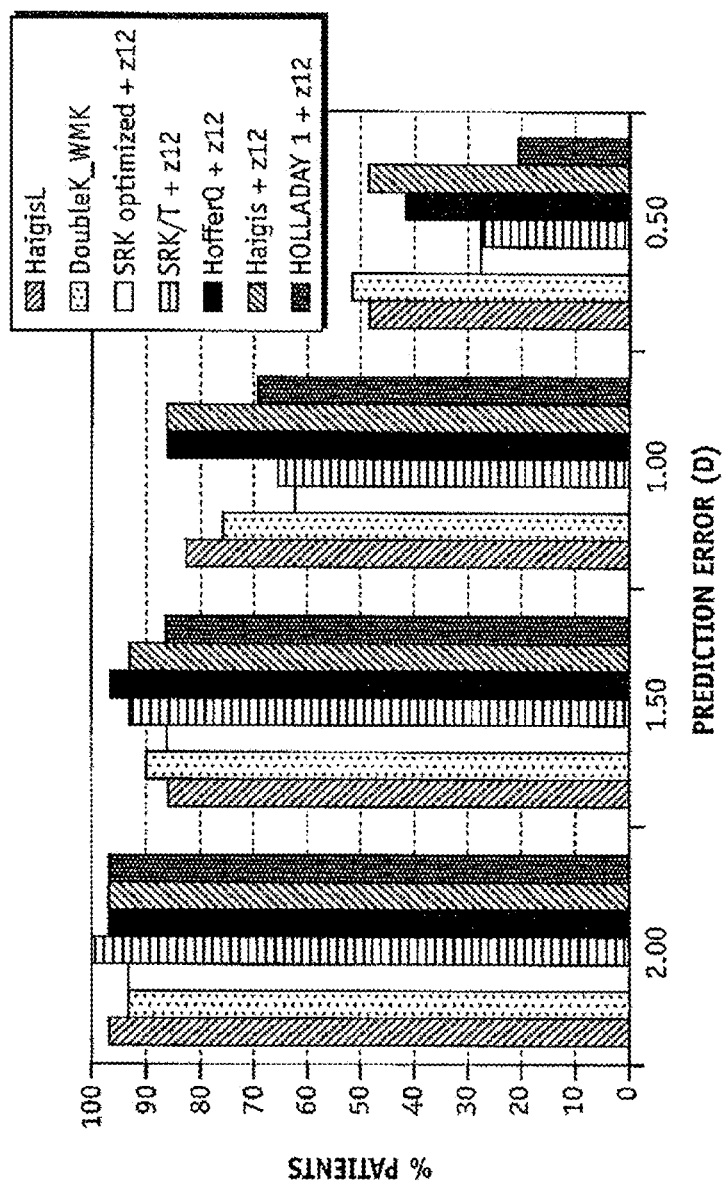
FIG. 25 shows the absolute IOL power prediction error in different ranges for different paraxial formulas considering corneal spherical aberration in comparison with the current state of art for postlasik patients.

In FIG. 25 the percentage of patients with different absolute prediction errors is shown for the different formulas. 86% of the patients are inside 1 D with Haigis+z12 or HofferQ+z12. 97% and 93% respectively can be calculated with accuracy better than 1.5 D, thus illustrating higher accuracy for these formulas incorporating corneal spherical aberration than those representing the current state of art for IOL power calculations in postlasik patients.

Figure 26:
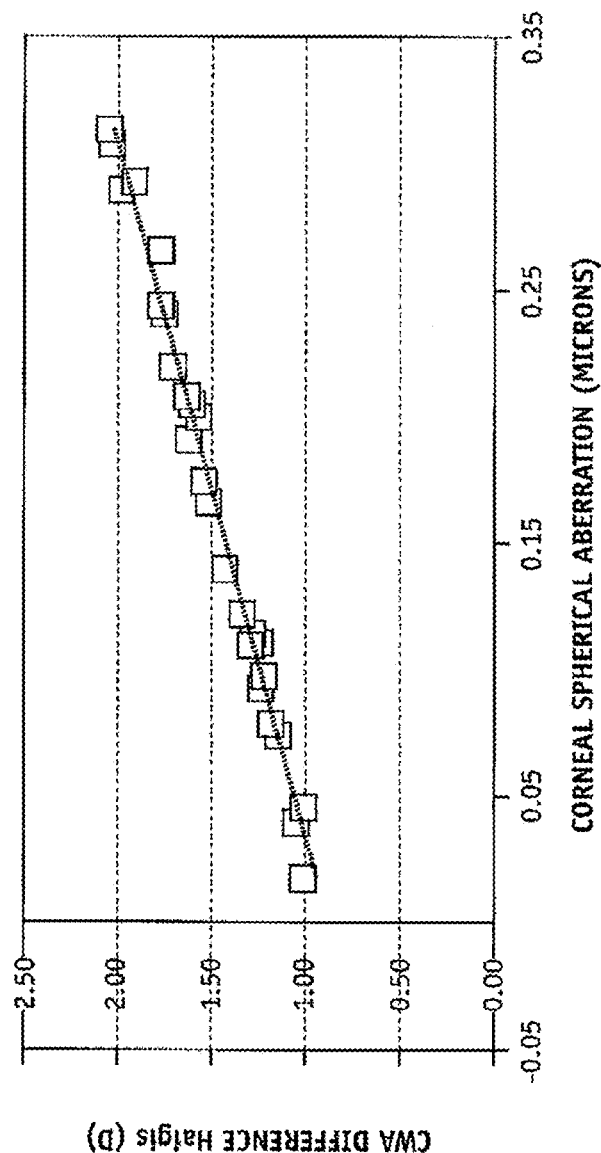
FIG. 26 illustrates difference between IOL power calculation for the Haigis formula considering spherical aberration and the Haigis paraxial formula versus corneal spherical aberration calculated at 4 mm pupil for postlasik patients.
Figure 27:
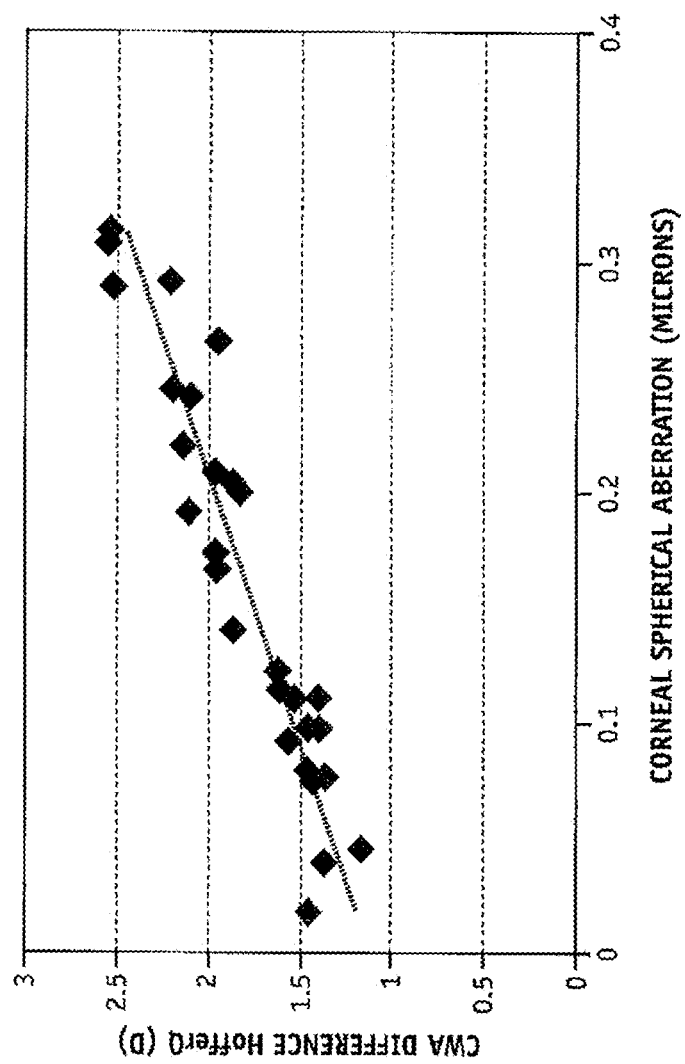
FIG. 27 illustrates difference between IOL power calculation for the HofferQ formula considering spherical aberration and the HofferQ paraxial formula versus corneal spherical aberration calculated at 4 mm pupil for postlasik patients.

FIG. 26 illustrates the IOL power prediction difference defined as Haigis+z12 formula result minus the regular Haigis formula result for each patient ("CWA difference Haigis"), which in the exemplary embodiments is by at least 1 Diopter. This difference increases with corneal spherical aberration up to 2 D. Similarly, FIG. 27 discloses the same behavior with respect to the HofferQ+z12 and HofferQ formulas, reaching in this case up to 2.5 D.

Thus, the present invention takes into consideration SA using simple linear regression to modify existing IOL power regression formulae to allow those existing IOL power regression formulae to be used for non-average patients, such as postlasik patients. Of course, the improvement in predictive accuracy depends on the base classical regression formula used, at least in that the modified SRK/T+z12 and Holladay 1+z12 provide results comparable with the current state of the art, and the HofferQ+z12 and Haigis+z12 modified formulae provide an appreciably improved predictive outcome as compared to the current state of the art.

It is important to be note that, just as the A constant is changed depending on the IOL model, the D constant may also need to be modified depending on the IOL model.

Of course, those skilled in the pertinent arts will appreciate, in light of the discussion herein, that the customized regression of the present invention developed at step 170 of methods 100 or 101 may include terms accounting for variables other than, or in addition to, the aforementioned accounting for SA. Such terms may account for other variables such as, for example, ACD, other aberrations, or the like, through the use of known conversions of those variables for use in a regression calculation or with a mathematical treatment other than a linear relationship. Other variable or aberrations may also include central corneal thickness (CCT) or related corneal pacyhymetry measurements, pupil diameter (PD), white to white distance (WTW), lens thickness (LT), axial length (AXL), retinal layer thickness (RLT), anterior corneal surface shape, posterior corneal surface shape, anterior lens surface shape, and posterior lens surface shape, lens tilt information and lens position information (including decentration) In some these embodiments, the biometric reader 301 would measure at least two biometric parameters and/or representations of aberrations, at least either being or being calculable for the variable, VA for which the customized regression is to be performed. As would be understood by those ordinarily skilled in the art, when the biometric parameter, VA, is used instead of the spherical aberration, SA, the variable VA may be substituted for the variable SA in Equations 1-8.

Figure 28:
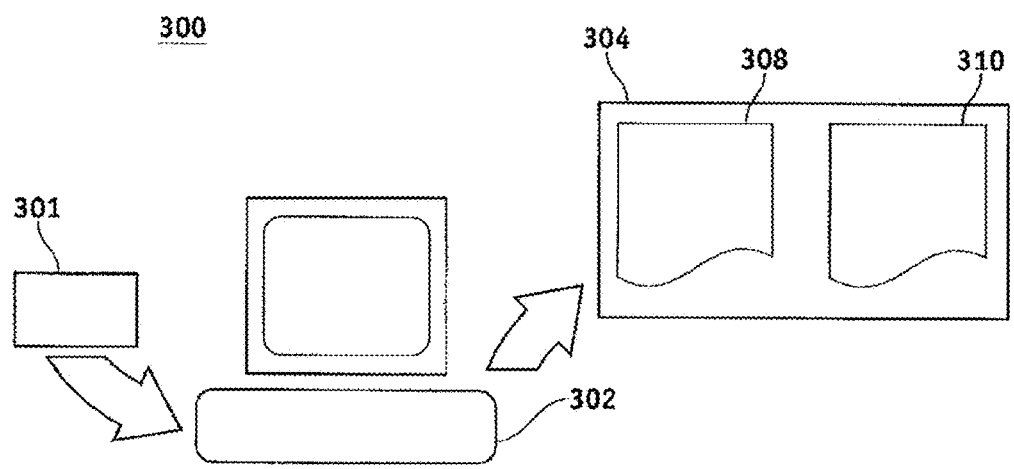
FIG. 28 is a block diagram illustrating the implementation of the present invention in a clinical system.

FIG. 28 is a block diagram illustrating the implementation of the present invention in a clinical system 300 comprised of one or more apparatuses that of capable of assessing the eye's biometry and of performing the calculations and comparisons set forth in methods 100 and 101, as well as the IOL power prediction set in procedure 200. The system 300 may include a biometric reader 301, a processor 302, and a computer readable memory 304 coupled to the processor 302. The computer readable memory 304 includes therein an array of ordered values 308 and sequences of instructions 310 which, when executed by the processor 302, cause the processor 302 to select an implantable IOL configured for implantation into the eye of the subject presenting the biometric readings to biometric reader 301, which feed the system with all the biometric data needed for the programmed calculation. The array of ordered values 308 may comprise data used or obtained from method 100 or 101 or other methods consistent with embodiments of the invention. For example, the array of ordered values 308 may comprise one or more desired refractive outcomes, parameters of an eye model based on one or more characteristics of at least one eye, and data related to an IOL or set of IOLs such as a power, an aspheric profile, and/or a lens plane.

The sequence of instructions 310 may include one or more steps of methods 100 and 101 or other methods consistent with embodiments of the invention. In some embodiments, the sequence of instructions 310 includes applying the custom regression of procedure 200, performing one or more calculations to determine the optimum IOL to implant achieving the desired outcome based on the formula obtained at the step 170.

The processor 302 may be embodied in a general purpose desktop or laptop computer, and/or may comprise hardware associated with biometric reader 301 specifically for selecting an IOL for placement into the eye of the subject. In certain embodiments, the system 300 may be configured to be electronically coupled to another device, such as one or more instruments for obtaining measurements of an eye or a plurality of eyes. From these measurements, methods 100 and/or 101 can be used to update the formula obtained at step 170. Alternatively, the system 300 may be embodied in a handheld device that may be adapted to be electronically and/or wirelessly coupled to one or more other devices.

FIGS. 29-32 illustrate another embodiment of an implementation of the present invention in a diagnostic measurement system 401 comprised of one or more apparatuses that are capable of assessing the eye's biometry and of performing the calculations and comparisons set forth in methods 100 and 101, as well as the IOL power prediction set in procedure 200. However, it should be understood that the principles involved in the diagnostic measurement system 40 1 and methods can be employed in a variety of other contexts, and therefore the novel devices and method disclosed and claimed here should not be construed as being limited to the example embodiments described below.

Biometric reader 301 and diagnostic measurement system preferably comprise one or more ophthalmic measurement subsystems configured to determine the optical and/or physical characteristics of a patient's eye, including the at least one selected biometric parameter. The biometric reader or ophthalmic measurement system may based on or perform similar functions to, those described, for instance, in "Optical Measurement Systems and Methods for Cataract Diagnostics and Treatment Planning", filed concurrently with this application, U.S. Pat. No. 7,988,290, entitled "Systems and Methods for Measuring the Shape and Location of an Object," which issued Aug. 2, 2011, and U.S. Pat. No. 8,260,024, entitled "Systems and Methods for Measuring Surface Shape," which issued Sep. 4, 2012, U.S. Pat. No. 8,126,246, filed Jan. 8, 2009, entitled "Systems And Methods For Measuring Surface Shape"; U.S. Pat. No. 8,260,024, filed Jan. 23, 2012, entitled "Systems And Methods For Measuring Surface Shape"; and European Patent Application No. 20090701204, filed Jan. 8, 2008, entitled "Systems And Methods For Measuring Surface Shape". These references are hereby incorporated herein by reference in their entirety.

Figure 29C:
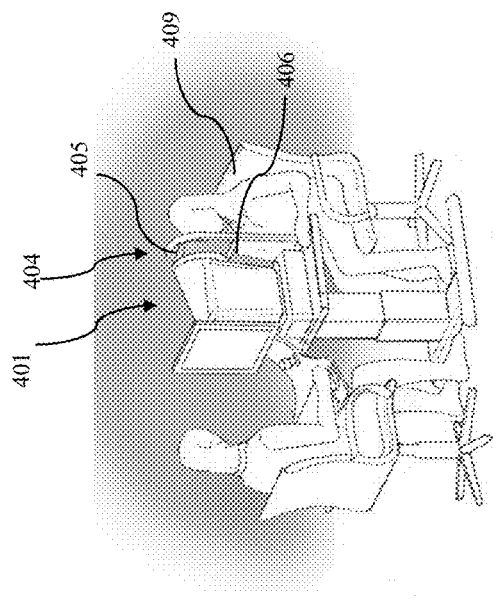
FIG. 29C illustrates a illustrates a side perspective view showing an optical measurement system according to many embodiments.
Figure 29A:
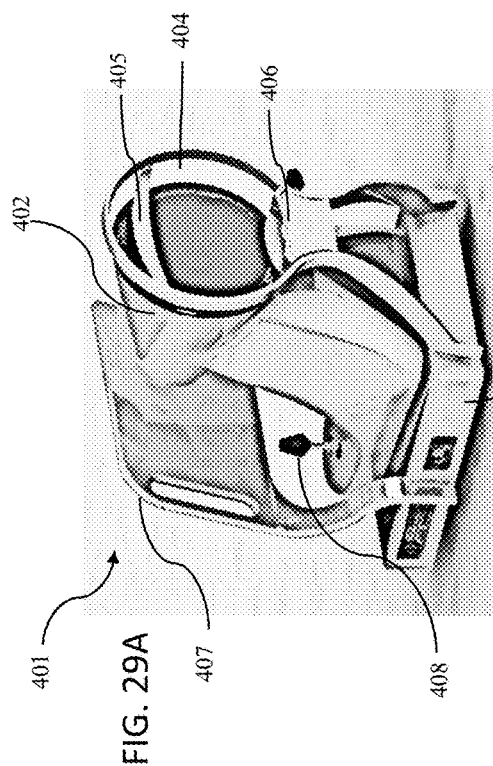
FIG. 29A illustrates a front perspective view showing an optical measurement system according to many embodiments.
Figure 29B:
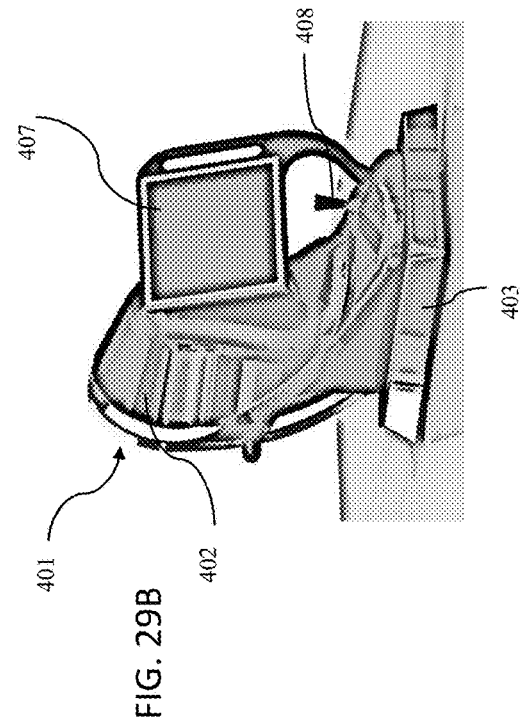
FIG. 29B illustrates a rear perspective view showing an optical measurement system according to many embodiments.

As shown in FIGS. 29A-29C, an optical measurement system 401, according to many embodiments, is operable to provide for a plurality of measurements of the human eye, including measurements of the cornea, the lens capsule, the lens and the retina. The main unit 402 comprises a base 403 and includes many primary subsystems of many embodiments of the system 401. For example, externally visible subsystems include a touch-screen display control panel 407, a patient interface assembly 404 and a joystick 408.

The patient interface 404 preferably includes one or more structures configured to hold a patient's head in a stable, immobile and preferably comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by the system 401.

In one embodiment the patient interface 404 includes a chin support 406 and/or a forehead rest 405 configured to hold the head of the patient in a single, uniform position suitably aligned with respect to the system 401 throughout the diagnostic measurement. As shown in FIG. 29C, the optical measurement system 401 is preferably disposed so that the patient may be seated in a patient chair 409. The patient chair 409 can be configured to be adjusted and oriented in three axes (x, y, and z) so that the patent's head can be at a suitable height and lateral position for placement on the patient interface.

In many embodiments, the system 401 may include external communication connections. For example, the system 401 can include a network connection (e.g., an RJ45 network connection) for connecting the system 401 to a network. The network connection can be used to enable network printing of diagnostic reports, remote access to view patient diagnostic reports, and remote access to perform system diagnostics. The system 401 can include a video output port (e.g., HDMI) that can be used to output video of diagnostic measurements performed by the system 401. The output video can be displayed on an external monitor for, for example, viewing by physicians or users. The output video can also be recorded for, for example, archival purposes. The system 401 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed at a later time for any suitable purpose such as, for example, printing from an external computer in the case where the user without access to network based printing or for use during cataract surgery, including laser cataract surgery.

Figure 30:
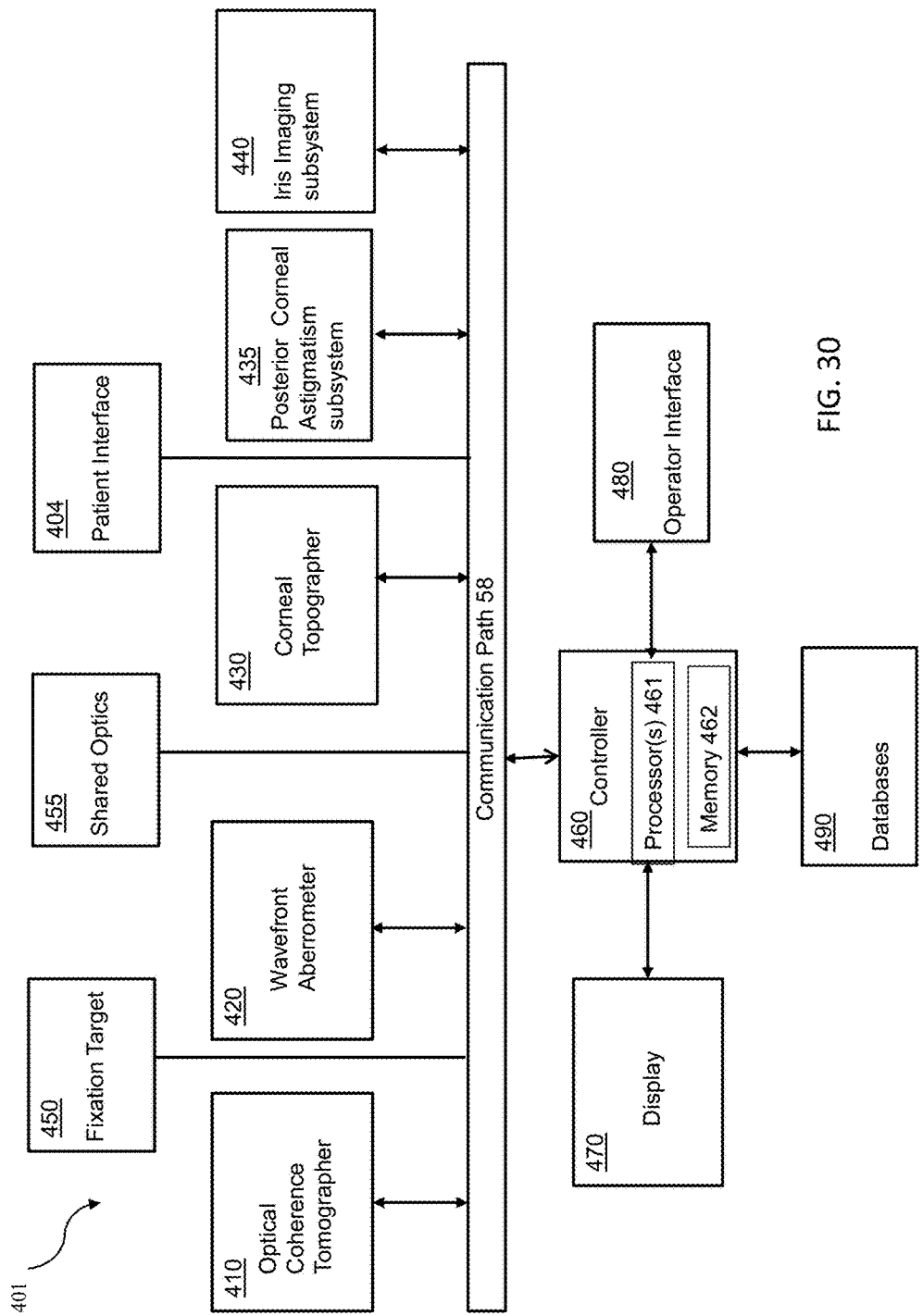
FIG. 30 is a block diagram of a system including an optical measurement instrument, and a position of an eye relative to the system according to one or more embodiments described herein which may be used by the optical measurement.

FIG. 30 is a block diagram of a system including an optical measurement instrument 401 according to one or more embodiments described herein. Optical measurement instrument 401 includes: an optical coherence tomographer (OCT) subsystem 410, a wavefront aberrometer subsystem 420, and a corneal topographer subsystem 430 for measuring one or more characteristics of a subject's eye. Optical measurement instrument 401 may further include an optional posterior corneal astigmatism subsystem 435, an iris imaging subsystem comprising a camera 440, a fixation target subsystem 450, a controller 460, including one or more processor(s) 461 and memory 462, a display 470 and an operator interface 480. Optical measurement instrument 401 further includes a patient interface 404 for a subject to present his or her eye for measurement by optical measurement instrument 401.

Optical coherence tomographer subsystem 410 is only one example of an eye structure imaging subsystem which may be employed in optical measurement instrument 401. In other embodiments, a different eye structure imaging subsystem may be employed, for example a Scheimplug Imager, a fluorescence imager, a structured lighting imager, a wavefront tomographer, an ultrasound imager and a plenoptic imager.

The wavefront aberrometer subsystem 420 is configured to measure ocular aberrations, preferably including low and high order aberrations, by measuring the wavefront emerging from the eye by, for example a Shack Hartman sensor. The measured shape of the imaged waveform can then be correlated to the surface profile of the patient's eye.

The wavefront analyzer may be based on interferometric systems, Shack-Hartmann wavefront sensors, or the like. Suitable Shack-Hartmann wavefront sensors are disclosed, for example, in U.S. Pat. No. 6,550,917 (Neal et al.), U.S. Pat. No. 6,130,419 (Neal), U.S. Pat. No. 6,052,180 (Neal et al.), or U.S. Pat. No. 5,777,718 (Williams et al.), all of which are hereby incorporated by reference in their entirety for all purposes as if fully set forth herein. A tomographer based on a Shack-Hartmann wavefront sensor may also be incorporated into the system, for example, as disclosed in U.S. Pat. No. 6,634,750, which is hereby incorporated by reference in its entirety for all purposes as if fully set forth herein.

Other suitable systems for the measurement of refractive error, and particularly to methods and techniques for compiling a top put graphic mapping of refractive errors include: U.S. Pat. No. 6,908,196, filed Feb. 21, 2003, entitled "System And Method For Performing Optical Corrective Procedures With Real-Time Feedback"; U.S. Pat. No. 7,455,407, filed Apr. 21, 2004, entitled "System And Method Of Measuring And Mapping Three Dimensional Structures"; U.S. Pat. No. 7,553,022, filed Jul. 27, 2007, entitled "System And Method Of Measuring And Mapping Three Dimensional Structures"; U.S. Pat. No. 7,988,292, filed May 29, 2009, entitled "System And Method Of Measuring And Mapping Three Dimensional Structures"; and WO2001/058339, filed Feb. 8, 2001, entitled "Dynamic Range Extension Techniques For A Wavefront Sensor." These references are hereby incorporated herein by reference in their entirety.

As used herein, the term "Helmholtz source" or "Helmholtz light source" means one or a plurality of individual sources or individual light sources disposed such that light from each of the individual light sources passes through an optical element having optical power, reflects off of a test object, passes through the optical element, and is received by a detector, wherein light from the Helmholtz source may be used to determine geometric and/or optical information of at least a portion of a surface of the test object. In general, it is a characteristic of Helmholtz sources that the signal at the detector is independent of the position of the test object relative to the Helmholtz source.

The corneal topographer subsystem 430 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 404.

In some embodiments, the corneal topographer subsystem may determine a shape of a surface of the patient's eye based upon a reflected pattern off a patient's eye. In some embodiments, the corneal topography subsystem may comprise a plurality of first elements disposed about a central axis. The pattern and the associated plurality of first elements may be considered a Placido-type source. As used herein, the term "Placido-type source" means a mask, pattern, or plurality of individual light sources disposed such that light from the source reflects off of a reference or test object (e.g. a patient's eye), passes through an imaging system, and is received by a detector, and, in some embodiments, the light from the Placido-type source passes only once through the imaging system. The individual light sources may be active sources generating light energy or apertures through which light energy is transmitted. Individual mask or pattern features may include lighter or more reflective portions of the mask or pattern configured to reflect light. As used herein, the terms "Placido disk" means a Placido-type source configured as a plurality of concentric rings or annular shapes.

Without being limited by any particular embodiment, the posterior corneal astigmatism assembly 435 is generally based on the principle that the amount of distortion of an object by a toric lens that is detected by a detector depends on a distance of the detector from the toric lens. More specifically, the amount of detected distortion increases with increasing distance from the toric lens. Thus, the simultaneous imaging by a near detector and far detector provides the total corneal astigmatism. To find the posterior corneal astigmatism, the anterior corneal astigmatism is subtracted from the total corneal astigmatism. This can be done, for instance, with vectoral methods to get the axis correct as is known to those ordinarily skilled. The amount of distortion seen by the far detector is proportional to the distance that the iris is from the apex of the cornea. As such, the accuracy of the total corneal astigmatism and posterior corneal astigmatism calculations can be improved if an accurately measured anterior chamber depth is included.

Fixation target system 450 is configured to control the patient's accommodation, because it is often desired to measure the refraction and wavefront aberrations when eye is focused at its far point Images captured by the corneal topographer subsystem 410, the wavefront aberrometer 420, the optical coherence tomographer subsystem 430 or the camera of the iris imaging subsystem 440 may be displayed with a display of the operator interface 480 of the optical measurement system 401 or the display 470 of the optical measurement system, respectively. The operator interface may also be used to modify, distort, or transform any of the displayed images.

Iris images obtained by the iris imaging subsystem may be used for registering and/or fusing the multiple data sets obtained by the various subsystems of the present invention, by methods described for instance in "Method for registering multiple data sets," U.S. patent application Ser. No. 12/418,841, which is incorporated herein by reference. As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, both patient movement between measurements (and/or during a measurement sequence) can be identified, as well as changes in the eye itself (including those induced by the measurement, such as changes in the size of the pupil, changes in pupil location, etc.).

In many embodiments, an optical measurement system according the present includes a target fixation subsystem. The Fixation target subsystem 450 is used to control the patient's accommodation, because it is often desired to measure the refraction and wavefront aberrations when eye is focused at its far point (e.g., because LASIK treatments are primarily based on this). Cylindrical correction and liquid lenses for the target path may also be used. In the target fixation subsystem, a projection of a target, for instance a cross-hair pattern is projected onto the eye of the patient, the cross hair pattern being formed by a backlit LED and a film. An alternative embodiment is to provide a video target that allows the projection of letters, charts, pictures or movies. One method to control accommodation is to provide the patient with a task "click a button each time you recognize a real word" or "click a button each time the target includes the color purple" in order to insure that the subject is really looking and concentrating on the target.

The shared optics 455 provide a common propagation path that is disposed between the patient interface 404 and each of the optical coherence tomographer (OCT) subsystem 410, the wavefront aberrometer subsystem 420, the corneal topographer subsystem 430, and in some embodiments, an optional posterior corneal astigmatism subsystem 435, the camera of the iris imaging subsystem 440, and the fixation target 450. In many embodiments, the shared optics 455 may comprise a number of optical elements, including mirrors, lenses and beam combiners to receive the emission from the respective subsystem to the patient's eye and, in some cases, to redirect the emission from a patient's eye along the common propagation path to an appropriate director.

The controller 460 controls the operation of the optical measurement instrument 401 and can receive input from any of the optical coherence tomographer (OCT) subsystem 410, the wavefront aberrometer subsystem 420, the corneal topographer subsystem 430 for measuring one or more characteristics of a subject's eye, the camera of the iris imaging subsystem 440, the fixation target 450, the display 470 and the operator interface 480 via the communication paths 458. The controller 460 can include any suitable components, such as one or more processor, one or more field-programmable gate array (FPGA), and one or more memory storage devices. In many embodiments, the controller 460 controls the display 470 to provide for user control over the laser eye surgery procedure for pre-cataract procedure planning according to user specified treatment parameters as well as to provide user control over the laser eye surgery procedure. The communication paths 58 can be implemented in any suitable configuration, including any suitable shared or dedicated communication paths between the controller 460 and the respective system components.

The operator interface 480 can include any suitable user input device suitable to provide user input to the controller 460. For example, the user interface devices 480 can include devices such as joystick 408, a keyboard or a touchscreen display 470.

The optical coherence tomography subsystem 410 is configured to measure the spatial disposition (e.g., three-dimensional coordinates such as X, Y, and Z of points on boundaries) of eye structures in three dimensions. In the optical coherence tomography subsystem 410, a z-scan device (not shown) is operable to alter the focus of the beam in the z-direction (i.e., along the direction of propagation of the OCT beam) under control of the controller, and an x-scan device (not shown), and a y-scan device (not shown) are operable to translate the OCT beam in the x and y directions (i.e., perpendicular to the direction of propagation of the of the OCT beam), respectively, under control of the controller. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by the controller for a number of purposes, including, in some embodiment to program and control a subsequent laser-assisted surgical procedure. The spatial disposition of the structures of interest and/or of suitable matching geometric modeling can also be used to determine a wide variety of parameters.

The OCT systems and methods of the present invention are preferably FD-OCT (Fourier domain optical coherence tomography) systems, including either an SD-OCT (spectral domain optical coherence tomography) system or, more preferably, an SS-OCT (swept source optical coherence tomography) system. In conventional FD-OCT systems, the interference signal is distributed and integrated over numerous spectral wavelength intervals, and is inverse Fourier transformed to obtain the depth-dependent reflectivity profile of the sample. The profile of scattering as a function of depth is referred to as an A-scan (Axial-scan). The beam can be scanned laterally to produce a set of A-scans that can be combined together to form a tomogram of the sample (a B-scan).

In an SD-OCT system, various spectral wavelength intervals of the combined returned light from the reference and sample arms are spatially encoded using, for instance, a collimator, diffraction grating, and a linear detector array. Resampling of the data obtained from the linear detector array is performed in order to correct for the nonlinear spatial mapping of wavenumbers. After resampling and subtraction of the dc background, the depth profile structural information is obtained by performing the inverse Fourier transform operation. In swept-source OCT, the broad bandwidth optical source is replaced by a rapid-scanning laser source. By rapidly sweeping the source wavelength over a broad wavelength range, and collecting all the scattering information at each wavelength and at each position, the composition of the collected signal is equivalent to the spectral-domain OCT technique. The collected spectral data is then inverse Fourier transformed to recover the spatial depth-dependent information.

FD-OCT suffers from an inherent sample-independent limited depth range, typically between 1 and 5 mm. One limitation flows from the fact that FD-OCT extracts depth information from the inverse Fourier transform of a spectral interferogram. Since the spectral interferogram can only be recorded as a real signal, its Fourier transform is necessarily Hermitian symmetric about the zero path length difference (ZPD) position. As a result, the positive and negative displacements about the ZPD cannot be unambiguously resolved, which gives rise to mirror image artifacts and generally halves the useable range. This is referred to as the complex conjugate ambiguity. Another limitation is a sensitivity fall-off which results in reduced sensitivity with increasing depth. Moreover, since the signal in OCT is derived only from backscattered photons, optical attenuation from absorption and scattering generally result in a useable imaging depth of about 1-4 mm.

Several "full range" OCT techniques have been developed that eliminate the complex conjugate artifacts to effectively double the measurement range around the ZPD position. These full range OCT techniques result in useable imaging depths of up to about 5 mm or even up to about 8 mm. Suitable full range techniques include methods that dither the reference leg length (M. Wijtkowski, et al, Opt. Lett. V27, #16, pg 1415, 2002), or that exploit phase dispersion compensation (Kottig, et al, Opt. Express V20, #22, pg 24925, 2012) to break the phase ambiguity.

As a non-limiting example, the system 401 can be configured to use a swept source OCT imaging system employing wavelengths of around 1060 nm with an 8 mm scan depth. The spatial disposition of the eye structures using optical coherence tomography should generally be measured while the patient is engaged with patient interface 404. The OCT scan depth is preferably between 8 and 50 mm, and the scan depth is preferably greater than about 24 mm or even 30 mm to achieve a full eyescan depth. The swept source wavelengths can be centered at wavelengths from 840 nm to 1310 nm.

The average axial length of the adult human eye is about 24 mm. Since the full range imaging depth of the OCT measurements are only about 5 mm to 8 mm, then OCT scanning of the present invention preferably provides for OCT scans at different depths of the eye that can be combined together to form a combined OCT image of the eye. The OCT measurements of the present invention preferably includes OCT imaging at various depths of the patient's eye for imaging 1) at least a portion of the retina, 2) at least a portion of the anterior portion of the eye, including at least a portion of the cornea (anterior and posterior), iris, and lens (anterior and posterior), and 3) performing axial eye length measurements.

FIGS. 31A-31C illustrate various aspects of the OCT subsystem 410 according to various aspects of the present invention. FIG. 31A illustrates a preferred scanning region for the OCT subsystem according to many embodiments of the present invention. The scanning region may be defined from starting point 601 to ending point 602 at the anterior portion of the eye extending in a direction transverse the direction of propagation of the OCT beam and also extending in a direction parallel to an axis defining the axial length of the eye to the posterior portion 604 of the eye. The lateral scanning region should generally be sufficiently large in the lateral direction to permit imaging of the central portion of the cornea, at least a portion of the iris, at least a portion of the lens and at least of the retina. It should be noted that a region 603 between the posterior portion of the lens and the surface of the retina may optionally not be scanned by OCT subsystem 410 because the portion 603 does not contain anatomical structure for 3D analysis.

FIG. 31B shows a representative graph of an intensity of an OCT signal of an OCT subsystem 410 according to many embodiments as a function of depth along the axis defining the axial length of the eye. The graph generally exhibits approximately four peaks having a complex structure: (1) a peak 610 having a doublet-like structure and generally corresponding to a location of the cornea; (2) a peak 620 having a doublet-like structure and generally corresponding to a location of an anterior surface of the lens; (3) a peak 630 having a complex structure generally corresponding to a location of a posterior surface of the lens; and (4) a peak 640 generally corresponding to a location of a retina. A distance between peak 610 and peak 640 can be used to calculate the axial length (AL) of the eye. Preferably, an OCT scan by OCT subsystem 410, including both an A-scan and B-scan, is conducted at least one location in the anterior portion of the eye (e.g., a location of a cornea, a location of an anterior surface of a lens and/or a location of a posterior surface of the lens) and at least one location in the posterior portion of the eye (e.g., at a location of a retina). In some embodiments, an OCT scan by the OCT subsystem 410, including both an A-Scan and a B-scan is performed at a location corresponding to each of a location of the cornea, a location of an anterior surface of the lens, a location of a posterior surface of the lens, and a location corresponding to a retina.

It should be noted that because the OCT subsystem 410 provides for the detection of various structures of the eye, including a location of the cornea, the OCT subsystem 410 may be used as a ranging system to precisely align the patient in relation to the optical measurement system 401 of the present invention. The use of the OCT as a ranging system can significantly improve accuracy of corneal topography measurements, including keratometry measurements, which are sensitive to misalignment of the corneal structures.

FIG. 31C shows a cross-section of an eye obtained by an optical measurement system of the present invention using an OCT subsystem according to the present invention.

The optical measurement instrument 401, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 462 associated with controller 460. The plurality of characteristics may be measured preoperatively, and where appropriate, intra-operatively, and postoperatively.

In some embodiments, memory 462 associated with controller 460 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement instrument 401, in conjunction with measurement data of a subject's eye obtained by optical measurement instrument 401, which may include specifying and/or selecting a particular IOL for a subject's eye. For example, one or more processors of optical measurement instrument 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

Figure 32:
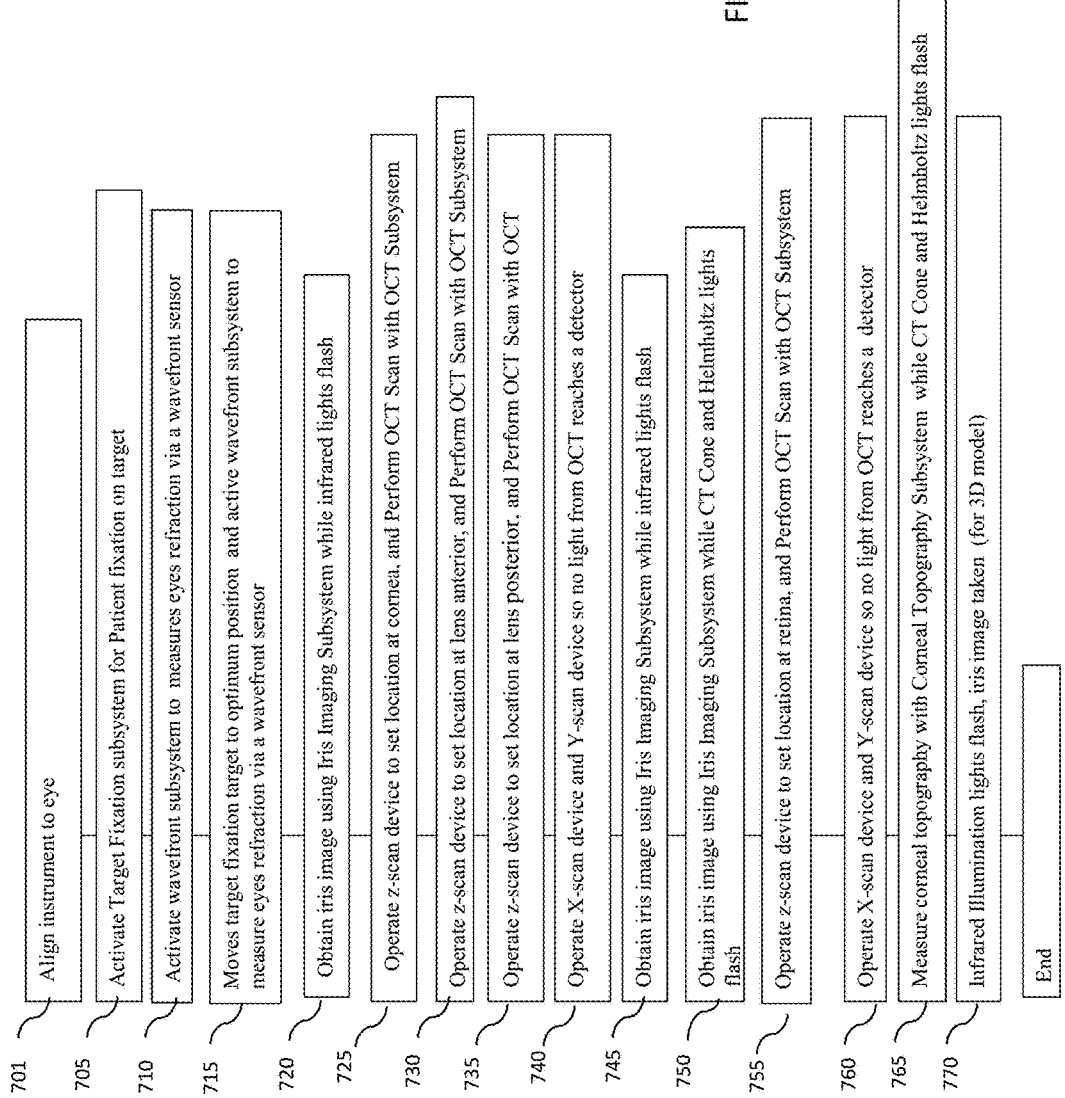
FIG. 32 is a flowchart of an example embodiment of a method for performing cataract diagnostics for an eye with an optical measurement instrument according to one embodiment described herein, including wavefront aberrometry, corneal topography and OCT measurements at various locations with the eye along the axial length of the eye.

FIG. 32 shows one embodiment of an operating sequence and method in which wavefront aberrometry measurements, corneal topography measurements and OCT measurements are all taken. The optical measurement apparatus, including the method of FIG. 32 may be used preoperatively, intraoperatively and/or postoperatively. In the method of FIG. 32, a step 701 comprises aligning the optical measurement system to the eye of the patent. A step 705 comprises activating the Target Fixation subsystem for patient fixation on target. A step 710 comprises activating the wavefront aberrometer subsystem such that the eye refraction is measured. A step 715 comprises activating the target fixation system to move the target to an optimum position and activating the wavefront aberrometer subsystem such that the eye refraction is measured. A step 720 comprises obtaining an iris image using Iris Imaging Subsystem. A step 725 comprises setting the OCT scan location at or near cornea, and performing an OCT Scan with the OCT Subsystem. A step 730 comprises setting the OCT location at a location at or near the lens anterior and performing an OCT Scan with the OCT Subsystem. A step 735 setting the OCT location at a location at or near the lens posterior and performing an OCT Scan with the OCT Subsystem. A step 740 comprises operating the X-scan device and Y-scan device so no light from OCT reaches an OCT detector. A step 745 comprises obtaining an iris image using Iris Imaging Subsystem. A step 750 comprises measuring the corneal topography with the Corneal Topography Subsystem. A step 755 comprises setting the OCT location at a location at or near the retina and performing an OCT Scan with the OCT Subsystem. A step 760 comprises operating OCT subsystem so that no light from OCT reaches detector. An optional step 765 comprises measure corneal topography with Corneal Topography Subsystem, which may provide for an improved 3D model of the patient eye. An optional step 770 comprises obtaining an iris image using Iris Imaging Subsystem (for 3D model).

Of course, not all of wavefront aberrometry measurements, corneal topography measurements and OCT measurements may need to be taken in operating the systems of the present invention. As such, the operating sequence and method of FIG. 32 may be altered as necessary to omit one or more of aberrometry measurements, corneal topography measurements, and OCT measurements, including the related iris image. Further, the operating sequence of FIG. 32 may be re-arranged to provide for a different order in which aberrometry measurements, corneal topography measurements and the OCT measurements are collected. Finally, OCT measurements utilizing the OCT subsystem and Iris images using the iris imaging subsystem may be taken simultaneously in order to improve three dimensional modeling of the patient's eye and improved iris registration of the measurement data sets.

Those of ordinary skill in the art may recognize that many modifications and variations of the present invention may be implemented without departing from the spirit or scope of the invention. Thus, it is intended that the present invention covers the modifications and variations of this invention provided they come within the scope of the discussion herein and any appended claims, and any equivalents thereto.

What is claimed is:

1. A system for predicting optical power for an intraocular lens based upon measured biometric parameters in a patient's eye, the system comprising:
a biometric reader capable of measuring one or more biometric parameters of the patient's eye and obtaining at least one value for at least one of the one or more biometric parameters, and further capable of measuring a representation of a corneal topography of the patient's eye;
a processor; and
a computer readable medium coupled to the processor and having stored thereon a program that upon execution causes the processor to: receive the at least one value; obtain a corneal spherical aberration (SA) based upon the measured representation of the corneal topography; and calculate an optimized optical power to obtain a desired postoperative condition by applying the received at least one value and the obtained corneal spherical aberration to a modified regression, wherein the modified regression is of the form:

optical power=$E+F*$(Classical Regression Formula)+$D*SA$, or optical power=$A+B*AXL+C*K+D*SA$, wherein E, F, D, A, B, and C are empirically derived factors across a plurality of other eyes, wherein AXL is an axial length of the patient's eye, wherein K is an average corneal power in diopters of the patient's eye, wherein the Classical Regression Formula is one of the SRK/T, Hoffer Q, Holladay1, Holladay 2, and Haigis regression formulas, and wherein the Classical Regression Formula employs the received at least one value.

2. The system of claim 1, further comprising a feedback input to said processor for modifying the modified regression in accordance with the optimized optical power.

3. The system of claim 1, wherein the one or more biometric parameters comprise at least one of: (a) central corneal thickness (CCT), an anterior chamber depth (ACD), a pupil diameter (PD), a white to white distance (WTW), a lens thickness (LT), the axial length (AXL), a retinal layer thickness (RLT), an anterior corneal surface shape, a posterior corneal surface shape, an anterior lens surface shape, a posterior lens surface shape, lens tilt information and lens position information.

4. The system of claim 1, wherein the one or more biometric parameters comprise at least one of: the axial length, an anterior chamber depth and a corneal power.

5. The system of claim 1, wherein the desired postoperative condition comprises a postoperative refraction.

6. The system of claim 1, wherein the biometric reader comprises a corneal topographer.

7. The system of claim 1, wherein the computer readable medium further has stored thereon a program that upon execution causes the processor to execute a ray tracing algorithm.

8. The system of claim 1, wherein the biometric reader comprises at least one of an optical wavefront sensor, a corneal topographer, an optical coherence tomographer, a Scheimpflug Imager, a fluorescence imager, a structured lighting imager, a wavefront tomographer, and an ultrasound imager.

9. The system of claim 1, wherein the program stored on the computer readable medium upon execution causes the processor to employ the modified regression employing measurements of the patient's eye where the patient's eye had previously undergone a refractive procedure.

10. A system for selecting an intraocular lens (IOL) for implantation based upon measured biometric parameters of a patient's eye, comprising:
a biometric reader capable of measuring one or more biometric parameters of the patient's eye and obtaining at least one value for at least one of the one or more biometric parameters, and further capable of measuring a representation of a corneal topography of the patient's eye;
a processor; and
a computer readable medium coupled to the processor and having stored thereon a program that upon execution causes the processor to: receive the at least one value; obtain a corneal spherical aberration (SA) based upon the measured representation of the corneal topography; and calculate an optimized IOL based upon a desired postoperative condition by applying the received at least one value and the obtained corneal spherical aberration to a modified regression, wherein the modified regression is of the form:

optical power=$E+F$*(Classical Regression Formula)+$D$*$SA$, or optical power=$A+B$*$AXL+C$*$K+D$*$SA$, wherein E, F, D, A, B, and C are empirically derived factors across a plurality of other eyes, wherein AXL is an axial length of the patient's eye, wherein K is an average corneal power in diopters of the patient's eye, wherein the Classical Regression Formula comprises one of the SRK/T, Hoffer Q, Holladay1, Holladay 2, and Haigis regression formulas, and wherein the Classical Regression Formula employs the received at least one value.

11. The system of claim 10, further comprising a feedback input to said process for modifying the modified regression in accordance with the optimized optical power.

12. The system of claim 10, wherein the one or more biometric parameters comprise at least one of: a central corneal thickness (CCT), anterior chamber depth (ACD), a pupil diameter (PD), a white to white distance (WTW), a lens thickness (LT), the axial length (AXL), a retinal layer thickness (RLT), an anterior corneal surface shape, a posterior corneal surface shape, an anterior lens surface shape, a posterior lens surface shape, lens tilt information and lens position information.

13. The system of claim 10, wherein the one or more biometric parameters comprise at least one of: the axial length, an anterior chamber depth and a corneal power.

14. The system of claim 10, wherein the desired postoperative condition comprises a postoperative refraction.

15. The system of claim 10, wherein biometric reader comprises a corneal topographer.

16. The system of claim 10, wherein the computer readable medium further has stored thereon a program that upon execution causes the processor to execute a ray tracing algorithm.

17. The system of claim 10, wherein the biometric reader comprises at least one of an optical wavefront sensor, a corneal topographer, an optical coherence tomographer, a Scheimpflug Imager, a fluorescence imager, a structured lighting imager, a wavefront tomographer, and an ultrasound imager.

18. The system of claim 10, wherein the program stored on the computer readable medium upon execution causes the processor to employ the modified regression employing measurements of the patient's eye where the patient's eye had previously undergone a refractive procedure.

19. A system for predicting optical power for an intraocular lens based upon measured biometric parameters of a patient's eye, comprising:
a biometric reader capable of measuring at least two biometric parameters of the patient's eye, including obtaining a first value (VA) for a first biometric parameter and a second value for a second biometric parameter;
a processor; and
a computer readable medium coupled to the processor and having stored thereon a program that upon execution causes the processor to receive the first and second values, and to calculate an optimized optical power to obtain a desired postoperative condition by applying the received first and second values to a modified regression, wherein the modified regression is of the form:

optical power=$E+F$*(Classical Regression Formula)+$D$*$VA$, wherein E, F and D are empirically derived factors across a plurality of other eyes, wherein the Classical Regression Formula comprises one of the SRK/T, Hoffer Q, Holladay1, Holladay 2, and Haigis regression formulas, and wherein the Classical Regression Formula employs the received first and second values.

20. The system of claim 19, further comprising a feedback input to said processor for modifying the modified regression in accordance with the optimized optical power.

21. The system of claim 19, wherein the at least two biometric parameters comprise at least one of: a central corneal thickness (CCT), anterior chamber depth (ACD), a pupil diameter (PD), a white to white distance (WTW), a lens thickness (LT), the axial length (AXL), a retinal layer thickness (RLT), an anterior corneal surface shape, a posterior corneal surface shape, an anterior lens surface shape, a posterior lens surface shape, lens tilt information and lens position information.

22. The system of claim 19, wherein the one or more biometric parameters comprise at least one of axial length, anterior chamber depth and corneal power.

23. The system of claim 19, wherein the desired postoperative condition comprises a postoperative refraction.

24. The system of claim 19, wherein the biometric reader comprises a corneal topographer.

25. The system of claim 19, wherein the computer readable medium further has stored thereon a program that upon execution causes the processor to execute a ray tracing algorithm.

26. The system of claim 19, wherein the biometric reader comprises at least one of an optical wavefront sensor, a corneal topographer, an optical coherence tomographer, a Scheimpflug Imager, a fluorescence imager, a structured lighting imager, a wavefront tomographer, and an ultrasound imager.

27. The system of claim 1, wherein the modified regression is of the form: optical power=E+F*(Classical Regression Formula)+D*SA.

28. The system of claim 10, wherein the modified regression is of the form: optical power=E+F*(Classical Regression Formula)+D*SA.

* * * * *